United States Patent
Schaub et al.

(10) Patent No.: US 8,785,693 B2
(45) Date of Patent: Jul. 22, 2014

(54) PROCESS FOR THE PREPARATION OF PRIMARY AMINES BY HOMOGENEOUSLY CATALYZED ALCOHOL AMINATION

(75) Inventors: Thomas Schaub, Neustadt (DE); Boris Buschhaus, Mannheim (DE); Marion Kristina Brinks, Mannheim (DE); Mathias Schelwies, Heidelberg (DE); Rocco Paciello, Bad Duerkheim (DE); Johann-Peter Melder, Boehl-Iggelheim (DE); Martin Merger, Frankenthal (DE)

(73) Assignee: BASF SE, Ludwigshafen (DE)

( * ) Notice: Subject to any disclaimer, the term of this patent is extended or adjusted under 35 U.S.C. 154(b) by 253 days.

(21) Appl. No.: 13/415,412

(22) Filed: Mar. 8, 2012

(65) Prior Publication Data

US 2012/0232292 A1 Sep. 13, 2012

Related U.S. Application Data

(60) Provisional application No. 61/450,147, filed on Mar. 8, 2011.

(51) Int. Cl.
| | | |
|---|---|---|
| C07C 209/16 | (2006.01) |
| C07C 209/18 | (2006.01) |
| C07D 265/30 | (2006.01) |
| C07D 241/04 | (2006.01) |
| C07D 295/00 | (2006.01) |
| C07D 207/18 | (2006.01) |
| C07D 207/06 | (2006.01) |
| C07D 295/02 | (2006.01) |
| C07D 317/00 | (2006.01) |

(52) U.S. Cl.
USPC ........... 564/480; 564/479; 544/106; 544/358; 548/565; 548/579; 549/492

(58) Field of Classification Search
None
See application file for complete search history.

(56) References Cited

U.S. PATENT DOCUMENTS

| | | |
|---|---|---|
| 3,275,554 A | 9/1966 | Wagenaar |
| 3,708,539 A | 1/1973 | Fenton |
| 3,751,475 A | 8/1973 | van der Voort et al. |
| 4,709,034 A | 11/1987 | Marsella |
| 4,832,702 A | 5/1989 | Kummer et al. |
| 4,942,261 A | 7/1990 | Ishimura et al. |
| 7,754,922 B2 | 7/2010 | Kubanek et al. |
| 2010/0331573 A1 | 12/2010 | Schaub et al. |
| 2011/0137029 A1 | 6/2011 | Kubanek et al. |
| 2011/0137030 A1 | 6/2011 | Kubanek et al. |
| 2011/0288337 A1 | 11/2011 | Chedid et al. |
| 2011/0294977 A1 | 12/2011 | Schaub et al. |
| 2012/0004464 A1 | 1/2012 | Huyghe et al. |
| 2012/0071692 A1 | 3/2012 | Ahrens et al. |
| 2012/0095221 A1 | 4/2012 | Wigbers et al. |
| 2012/0157715 A1 | 6/2012 | Pape et al. |

FOREIGN PATENT DOCUMENTS

| | | |
|---|---|---|
| DE | 2 125 039 A | 12/1971 |
| DE | 36 11 230 A1 | 10/1987 |
| EP | 0 234 401 A1 | 9/1987 |
| EP | 0 320 269 A2 | 6/1989 |
| EP | 0 696 572 A1 | 2/1996 |
| WO | WO 03/051508 A1 | 6/2003 |
| WO | WO 2008/006752 A1 | 1/2008 |
| WO | WO 2010/018570 A1 | 2/2010 |
| WO | WO 2011/067199 A1 | 6/2011 |
| WO | WO 2011/067200 A1 | 6/2011 |
| WO | WO 2011/082967 A1 | 7/2011 |
| WO | WO 2011/151268 A1 | 12/2011 |
| WO | WO 2011/155710 A1 | 12/2011 |
| WO | WO 2012/000952 A1 | 1/2012 |
| WO | WO 2012/034933 A1 | 3/2012 |
| WO | WO 2012/049101 A1 | 4/2012 |

OTHER PUBLICATIONS

U.S. Appl. No. 13/948,736, filed Jul. 23, 2013, Schelwies, et al.
U.S. Appl. No. 13/516,521, filed Jun. 15, 2012, Maegerlein, et al.
U.S. Appl. No. 13,158,667, Wigbers, et al.
U.S. Appl. No. 13/415,466, filed Mar. 8, 2012, Schaub, et al.
U.S. Appl. No. 13/415,174, filed Mar. 8, 2012, Schaub, et al.
U.S. Appl. No. 13/415,409, filed Mar. 8, 2012, Schaub, et al.
Yoshihisa Watanabe, et al., "The Ruthenium Catalyzed N-Alkylation and N-Heterocyclization of Aniline Using Alcohols and Aldehydes", Tetrahedron Letters, vol. 22, No. 28, 1981, pp. 2667-2670.
Sebastian Imm, et al., "Selective Ruthenium-Catalyzed Alkylation of Indoles by Using Amines", Chem. Eur. J., 16, DOI:10.1002/chem.200903261, 2010, pp. 2705-2709.
Annegret Tillack, et al., "A novel ruthenium-catalyzed amination of primary and secondary alcohols", Tetrahedron Letters, 47, 2006, pp. 8881-8885.
Dirk Hollmann, et al., "A General Ruthenium-Catalyzed Synthesis of Aromatic Amines", Angew. Chem. Int. Ed., 46, 2007, pp. 8291-8294.
Annegret Tillack, et al., "Salt-Free Synthesis of Tertiary Amines by Ruthenium-Catalyzed Amination of Alcohols", Eur. J. Org. Chem., 2008, pp. 4745-4750.
M. Haniti S. A. Hamid, et al., "Ruthenium-Catalyzed N-Alkylation of Amines and Sulfonamides Using Borrowing Hydrogen Methodology", J. Am. Chem. Soc., vol. 131, No. 5, 2009, pp. 1766-1774.

(Continued)

Primary Examiner — Brian J Davis
(74) Attorney, Agent, or Firm — Oblon, Spivak, McClelland, Maier & Neustadt, L.L.P.

(57) ABSTRACT

Process for the preparation of primary amines which have at least one functional group of the formula ($-CH_2-NH_2$) by alcohol amination of starting materials which have at least one functional group of the formula ($-CH_2-OH$), with ammonia, with the elimination of water, where the alcohol amination is carried out under homogeneous catalysis in the presence of at least one complex catalyst which comprises at least one element selected from groups 8 and 9 of the Periodic Table of the Elements, and also at least one phosphorus donor ligand of the general formula (I).

20 Claims, No Drawings

(56) References Cited

OTHER PUBLICATIONS

Ourida Saidi, et al., "Iridium-catalysed amine alkylation with alcohols in water", Chem. Commun., 46, 2010, 1541-1543.

Alessandro Del Zotto, et al., "Cyclopentadienyl Ru$^{II}$ Complexes as Highly Efficient Catalysts for the N-Methylation of Alkylamines by Methanol", Eur. J. Inorg. Chem., 2004, pp. 524-529.

Ken-ichi Fujita, et al., "N-Alkylation of amines with alcohols catalyzed by a Cp*Ir Complex", Tetrahedron Letters, 44, 2003, pp. 2687-2690.

Yoshihisa Watanabe, et al., "Ruthenium Complex-Controlled Catalytic N-Mono- or N,N-Dialkylation of Heteroaromatic Amines with Alcohols", J. Org. Chem., vol. 61, No. 13, 1996, pp. 4214-4218.

Benoît Blank, et al., "An Efficient Method for the Selective Iridium-Catalyzed Monoalkylation of (Hetero)aromatic Amines with Primary Alcohols", Adv. Synth. Catal., 350, 2008, pp. 749-758.

Ana Martinez-Asencio, et al., "N-Alkylation of poor nucleophilic amine and sulfonamide derivatives with alcohols by a hydrogen autotransfer process catalyzed by copper(II) acetate", Tetrahedron Letters, 51, 2010, pp. 325-327.

Sebastian Imm, et al., "Eine effiziente und allgemeine Synthese primärer Amine durch Ruthenium-katalysierte Aminierung sekundärer Alkohole mit Ammoniak", Angew. Chem., 122, 2010, pp. 8303-8306.

Dennis Pingen, et al., "Direkte Aminierung von sekundären Alkoholen mit Ammoniak", Angew. Chem., 122, 2010, pp. 8307-8310.

Chidambaram Gunanathan, et al., "Selective Synthesis of Primary Amines Directly from Alcohols and Ammonia", Angew. Chem. Int. Ed., 47, 2008, pp. 8661-8664.

Ryoko Kawahara, et al., "Multialkylation of Aqueous Ammonia with Alcohols Catalyzed by Water-Soluble Cp*Ir-Ammine Complexes", J. Am. Chem. Soc., vol. 132, No. 43, DOI: 10.1021/ja107274w, 2010, pp. 15108-15111.

PROCESS FOR THE PREPARATION OF PRIMARY AMINES BY HOMOGENEOUSLY CATALYZED ALCOHOL AMINATION

This patent application claims the benefit of U.S. provisional patent application Ser. No. 61/450,147 filed on Mar. 8, 2011, incorporated in its entirety herein by reference.

The present invention relates to a process for the preparation of primary amines by alcohol amination of primary alcohols with ammonia, with the elimination of water, in the presence of a complex catalyst which comprises at least one element selected from groups 8 and 9 of the Periodic Table of the Elements and also at least one phosphorus donor ligand of the general formula (I).

Primary amines are valuable products with a large number of different uses, for example as solvents, stabilizers, for the synthesis of chelating agents, as starting materials for producing synthetic resins, inhibitors, interface-active substances, intermediates in the manufacture of fuel additives (U.S. Pat. No. 3,275,554 A, DE 2125039 A and DE 36 11 230 A), surfactants, drugs and crop protection agents, hardeners for epoxy resins, catalysts for polyurethanes, intermediates for producing quaternary ammonium compounds, plasticizers, corrosion inhibitors, synthetic resins, ion exchangers, textile auxiliaries, dyes, vulcanization accelerators and/or emulsifiers.

Primary amines are currently prepared by the heterogeneously catalyzed alcohol amination of alcohols with ammonia. WO 2008/006752 A1 describes a process for the preparation of amines by reacting primary alcohols with ammonia in the presence of a heterogeneous catalyst which comprises zirconium dioxide and nickel. WO 03/051508 A1 relates to a process for the amination of alcohols using specific heterogeneous Cu/Ni/Zr/Sn catalysts. EP 0 696 572 A1 discloses nickel oxide-, copper oxide-, zirconium oxide- and molybdenum oxide-comprising heterogeneous catalysts for the amination of alcohols with ammonia and hydrogen. In the documents cited above, the reactions are carried out at temperatures in the range from 150 to 210° C. and ammonia pressures in the range from 30 to 200 bar.

The homogeneously catalyzed amination of monoalcohols with primary and secondary amines has been known since the 1970s where, in most cases, ruthenium or iridium catalysts are described. Compared to heterogeneously catalyzed reactions, the homogeneously catalyzed amination proceeds at significantly lower temperatures of from 100 to 150° C. The reaction of alcohols with primary and secondary amines is described, for example, in the following publications: U.S. Pat. No. 3,708,539; Y. Watanabe, Y. Tsuji, Y. Ohsugi, Tetrahedron Lett. 1981, 22, 2667-2670; S. Bähn, S. Imm, K. Mevius, L. Neubert, A. Tillack, J. M. J. Williams, M. Beller, Chem. Eur. J. 2010, DOI: 10.1002/chem. 200903144; A. Tillack, D. Hollmann, D. Michalik, M. Beller, Tetrahedron Lett. 2006, 47, 8881-8885; D. Hollmann, S. Bähn, A. Tillack, M. Beller, Angew. Chem. Int. Ed. 2007, 46, 8291-8294; A. Tillack, D. Hollmann, K. Mevius, D. Michalik, S. Bähn, M. Beller, Eur. J. Org. Chem. 2008, 4745-4750; M. H. S. A. Hamid, C. L. Allen, G. W. Lamb, A. C. Maxwell, H. C. Maytum, A. J. A. Watson, J. M: J. Williams, J. Am. Chem. Soc. 2009, 131, 1766-1774; O. Saidi, A. J. Blacker, M. M. Farah, S. P. Marsden, J. M. J. Williams, Chem. Commun. 2010, 46, 1541-1543; A. Tillack, D. Hollmann, D. Michalik, M. Beller, Tet. Lett. 2006, 47, 8881-8885; A. Del Zlotto, W. Baratta, M. Sandri, G. Verardo, P. Rigo, Eur. J. Org. Chem. 2004, 524-529; A. Fujita, Z. Li, N. Ozeki, R. Yamaguchi, Tetrahedron Lett. 2003, 44, 2687-2690; Y. Watanabe, Y. Morisaki, T. Kondo, T. Mitsudo, J. Org. Chem. 1996, 61, 4214-4218, B. Blank, M. Madalska, R. Kempe, Adv. Synth. Catal. 2008, 350, 749-750, A. Martinez-Asencio, D. J. Ramon, M. Yus, Tetrahedron Lett. 2010, 51, 325-327. The greatest disadvantage of the systems described above is that with these processes only the amination of alcohols with primary and secondary amines, with the formation of secondary and tertiary amines, is possible. The reaction of alcohols with ammonia, which is the economically most attractive amination reaction, is not described in these works.

S. Imm, S. Bähn, L. Neubert, H. Neumann, M. Beller, Angew. Chem. 2010, 122, 8303-8306 and D. Pingen, C. Müller, D. Vogt, Angew. Chem. 2010, 122, 8307-8310 describe the amination of secondary alcohols such as cyclohexanol with ammonia homogeneously catalyzed with ruthenium catalysts. EP 0 320 269 A2 discloses the palladium-catalyzed amination of primary allyl alcohols with ammonia to give primary alkylamines. WO 2010/018570 and C. Gunanathan, D. Milstein, Angew. Chem. Int. Ed. 2008, 47, 8661-8664 describe the amination of primary alcohols with ammonia to give primary amines with the help of a specific ruthenium catalyst with acridine-based pincer ligands.

R. Kawahara, K. I. Fujita, R. Yamaguchi, J. Am. Chem. Soc. DOI: 10.1021/ja107274w describes the amination of primary alcohols with ammonia using an iridium catalyst which has, as ligands, Cp* (1,2,3,4,5-pentamethylcyclopentadienyl) and ammonia. However, using the catalyst system described therein, when reacting primary alcohols with ammonia, the undesired tertiary amines are exclusively obtained.

EP 0 234 401 A1 describes the reaction of diethylene glycol with ammonia in the presence of a ruthenium carbonyl compound. In the process described in EP 0 234 401 A1, the monoamination product (monoethanolamine) is formed. However, it is disadvantageous that the secondary and tertiary amines (di- and triethanolamine) and cyclic products (N-(hydroxyethyl)piperazine and N,N'-bis(hydroxyethyl)piperazine) are formed as by-products.

Although the prior art describes processes for the homogeneously catalyzed reaction of primary alcohols to give primary amines, there is still a great need for alternative, improved preparation processes with simpler and readily accessible phosphane ligands.

It is an object of the present invention to provide a process for the preparation of primary amines by homogeneously catalyzed alcohol amination of primary alcohols with ammonia, with the elimination of water, in which no acridine-based complex catalyst is used and in which the formation of undesired by-products, such as secondary and tertiary amines and also cyclic amines, is largely avoided.

The object is achieved by a process for the preparation of primary amines which have at least one functional group of the formula ($-CH_2-NH_2$) by alcohol amination of starting materials which have at least one functional group of the formula ($-CH_2-OH$), with ammonia, with the elimination of water, where the alcohol amination is carried out under homogeneous catalysis in the presence of at least one complex catalyst which comprises at least one element selected from groups 8 and 9 of the Periodic Table of the Elements, and also at least one phosphorus donor ligand of the general formula (I),

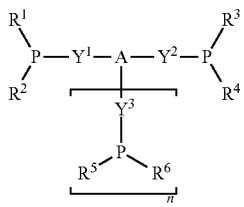

where
n is 0 or 1;
$R^1$, $R^2$, $R^3$, $R^4$, $R^5$, $R^6$ are, independently of one another, unsubstituted or at least monosubstituted $C_1$-$C_{10}$-alkyl, $C_1$-$C_4$-alkyldiphenylphosphine (—$C_1$-$C_4$-alkyl-P(phenyl)$_2$), $C_3$-$C_{10}$-cycloalkyl, $C_3$-$C_{10}$-heterocyclyl comprising at least one heteroatom selected from N, O and S, $C_5$-$C_{14}$-aryl or $C_5$-$C_{10}$-heteroaryl comprising at least one heteroatom selected from N, O and S,
where the substituents are selected from the group consisting of:
F, Cl, Br, OH, CN, $NH_2$ and $C_1$-$C_{10}$-alkyl;
A is
i) a bridging group selected from the group unsubstituted or at least monosubstituted N, O, P, $C_1$-$C_6$-alkane, $C_3$-$C_{10}$-cycloalkane, $C_3$-$C_{10}$-heterocycloalkane comprising at least one heteroatom selected from N, O and S, $C_5$-$C_{14}$-aromatic and $C_5$-$C_6$-heteroaromatic comprising at least one heteroatom selected from N, O and S,
where the substituents are selected from the group consisting of:
$C_1$-$C_4$-alkyl, phenyl, F, Cl, Br, OH, $OR^7$, $NH_2$, $NHR^7$ or $N(R^7)_2$,
where $R^7$ is selected from $C_1$-$C_{10}$-alkyl and $C_5$-$C_{10}$-aryl; or
ii) a bridging group of the formula (II) or (III):

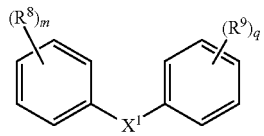

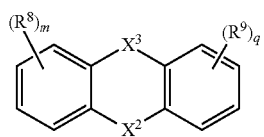

m, q are, independently of one another, 0, 1, 2, 3 or 4;
$R^8$, $R^9$ are, independently of one another, selected from the group $C_1$-$C_{10}$-alkyl, F, Cl, Br, OH, $OR^7$, $NH_2$, $NHR^7$ and $N(R^7)_2$,
where $R^7$ is selected from $C_1$-$C_{10}$-alkyl and $C_5$-$C_{10}$-aryl;
$X^1$, $X^2$ are, independently of one another, NH, O or S;
$X^3$ is a bond, NH, $NR^{10}$, O, S or $CR^{11}R^{12}$;
$R^{10}$ is unsubstituted or at least monosubstituted $C_1$-$C_{10}$-alkyl, $C_3$-$C_{10}$-cycloalkyl, $C_3$-$C_{10}$-heterocyclyl comprising at least one heteroatom selected from N, O and S, $C_5$-$C_{14}$-aryl or $C_5$-$C_{10}$-heteroaryl comprising at least one heteroatom selected from N, O and S,
where the substituents are selected from the group consisting of: F, Cl, Br, OH, CN, $NH_2$ and $C_1$-$C_{10}$-alkyl;
$R^{11}$, $R^{12}$ are, independently of one another, unsubstituted or at least monosubstituted $C_1$-$C_{10}$-alkyl, $C_1$-$C_{10}$-alkoxy, $C_3$-$C_{10}$-cycloalkyl, $C_3$-$C_{10}$-cycloalkoxy, $C_3$-$C_{10}$-heterocyclyl comprising at least one heteroatom selected from N, O and S, $C_5$-$C_{14}$-aryl, $C_5$-$C_{14}$-aryloxy or $C_5$-$C_{10}$-heteroaryl comprising at least one heteroatom selected from N, O and S,
where the substituents are selected from the group consisting of: F, Cl, Br, OH, CN, $NH_2$ and $C_1$-$C_{10}$-alkyl;
$Y^1$, $Y^2$, $Y^3$ are, independently of one another, a bond, unsubstituted or at least monosubstituted methylene, ethylene, trimethylene, tetramethylene, pentamethylene or hexamethylene,
where the substituents are selected from the group consisting of: F, Cl, Br, OH, $OR^7$, CN, $NH_2$, $NHR^7$, $N(R^7)_2$ and $C_1$-$C_{10}$-alkyl,
where $R^7$ is selected from $C_1$-$C_{10}$-alkyl and $C_5$-$C_{10}$-aryl.

Surprisingly, it has been found that with the complex catalysts used in the process according to the invention which comprise at least one element selected from groups 8 and 9 of the Periodic Table of the Elements and also at least one phosphorus donor ligand of the general formula (I), primary amines are obtained in considerably improved yields compared with the processes described in the prior art. Moreover, the formation of undesired by-products, such as secondary and tertiary amines and also cyclic amines, is largely avoided.

Starting Materials

In the process according to the invention, alcohols which have at least one functional group of the formula (—$CH_2$—OH) are used as starting materials.

Suitable starting materials are practically all alcohols which satisfy the prerequisites specified above. The alcohols may be straight-chain, branched or cyclic. Moreover, the alcohols can carry substituents which exhibit inert behavior under the reaction conditions of the alcohol amination, for example alkoxy, alkenyloxy, alkenyloxy, alkylamino, dialkylamino and halogens (F, Cl, Br, I). According to the invention, besides monoalcohols, also diols, triols, polyols and alkanolamines which have at least one functional group of the formula (—$CH_2$—OH) can be used as starting materials.

Monoalcohols to be used according to the invention are alcohols which have only one functional group of the formula (—$CH_2$—OH). Diols, triols and polyols to be used according to the invention are alcohols which have at least one functional group of the formula (—$CH_2$—OH) and one, two or more further hydroxyl groups. Alkanolamines to be used according to the invention are compounds which have at least one functional group of the formula (—$CH_2$—OH) and at least one further primary, secondary or tertiary amino group.

Suitable alcohols are, for example, those of the general formula (IV):

$$R^a\text{—}CH_2\text{—}OH \qquad (IV),$$

where
$R^a$ is selected from the group hydrogen, unsubstituted or at least monosubstituted $C_1$-$C_{30}$-alkyl, $C_3$-$C_{10}$-cycloalkyl, $C_3$-$C_{10}$-heterocyclyl comprising at least one heteroatom selected from N, O and S, $C_5$-$C_{14}$-aryl and $C_5$-$C_{14}$-heteroaryl comprising at least one heteroatom selected from N, O and S, where the substituents are selected from the group consisting of: F, Cl, Br, OH, OR$^7$, CN, NH$_2$, NHR$^7$ or N(R$^7$)$_2$, C$_1$-C$_{10}$-alkyl, C$_3$-C$_{10}$-cycloalkyl, C$_3$-C$_{10}$-heterocyclyl comprising at least one heteroatom selected from N, O and S, C$_5$-C$_{14}$-aryl and C$_5$-C$_{14}$-heteroaryl comprising at least one heteroatom selected from N, O and S, where R$^7$ is selected from C$_1$-C$_{10}$-alkyl and C$_5$-C$_{10}$-aryl.

Preferably, for example, the following alcohols are aminated: methanol, ethanol, n-propanol, n-butanol, isobutanol, n-pentanol, n-hexanol, n-heptanol, n-octanol, n-nonanol, 2-ethylhexanol, tridecanol, stearyl alcohol, palmityl alcohol, benzyl alcohol, 2-phenylethanol, 2-(p-methoxyphenyl)ethanol, 2-(3,4-dimethoxyphenyl)ethanol, allyl alcohol, propargyl alcohol, 2-hydroxymethyl-furan, lactic acid and serine.

Starting materials which can be used are all known diols which have at least one functional group of the formula (—CH$_2$—OH). Examples of diols which can be used as starting materials in the process according to the invention are 1,2-ethanediol (ethylene glycol), 1,2-propanediol (1,2-propylene glycol), 1,3-propanediol (1,3-propylene glycol), 1,4-butanediol (1,4-butylene glycol), 1,2-butanediol (1,2-butylene glycol), 2,3-butanediol, 2-methyl-1,3-propanediol, 2,2-dimethyl-1,3-propanediol (neopentyl glycol), 1,5-pentanediol, 1,2-pentanediol, 1,6-hexanediol, 1,2-hexanediol, 1,7-heptanediol, 1,2-heptanediol, 1,8-octanediol, 1,2-octanediol, 1,9-nonanediol, 1,2-nonanediol, 1,10-decanediol, 2,4-dimethyl-2,5-hexanediol, hydroxypivalic acid neopentyl glycol ester, diethylene glycol, triethylene glycol, 2-butene-1,4-diol, 2-butyne-1,4-diol, polyethylene glycols, polypropylene glycols, such as 1,2-polypropylene glycol and 1,3-polypropylene glycol, polytetrahydrofuran, diethanolamine, 1,4-bis(2-hydroxyethyl)piperazine, diisopropanolamine, N-butyldiethanolamine, 2,5-(dimethanol)-furan, 1,4-bis(hydroxymethyl)cyclohexane and N-methyldiethanolamine. 2,5-(dimethanol)-furan is also called 2,5-bis(hydroxymethyl)-furan.

Preference is given to diols which have two functional groups of the formula (—CH$_2$—OH).

Particularly preferred diols are 1,2-ethanediol (ethylene glycol), 1,2-propanediol (1,2-propylene glycol), 1,3-propanediol (1,3-propylene glycol), 1,4-butanediol (1,4-butylene glycol), 2-methyl-1,3-propanediol, 2,2-dimethyl-1,3-propanediol (neopentyl glycol), 1,5-pentanediol, 1,6-hexanediol, 1,7-heptanediol, 1,8-octanediol, 1,9-nonanediol, diethylene glycol, triethylene glycol, polyethylene glycols, polypropylene glycols, such as 1,2-polypropylene glycol and 1,3-polypropylene glycol, polytetrahydrofuran, diethanolamine, diisopropanolamine, N-butyldiethanolamine, 2,5-(dimethanol)-furan and N-methyldiethanolamine.

Starting materials which can be used are all known triols which have at least one functional group of the formula (—CH$_2$—OH). Examples of triols which can be used as starting materials in the process according to the invention are glycerol, trimethylolpropane and triethanolamine.

Preference is given to triols which have at least two functional groups of the formula (—CH$_2$—OH).

Particularly preferred triols are glycerol and triethanolamine.

Starting materials which can be used are all known polyols which have at least one functional group of the formula (—CH$_2$—OH). Examples of polyols which can be used as starting materials in the process according to the invention are 2,2-bis(hydroxymethyl)-1,3-propanediol (pentaerythritol), sorbitol, inositol, sugars and polymers with primary hydroxyl groups (—CH$_2$—OH) such as, for example, glucose, mannose, fructose, ribose, deoxyribose, galactose, N-acetylglucosamine, fucose, rhamnose, sucrose, lactose, cellobiose, maltose and amylose, cellulose, starch and xanthan.

Preference is given to polyols which have at least two functional groups of the formula (—CH$_2$—OH).

Particularly preferred polyols are cellulose, polyvinyl alcohol and glucose.

Starting materials which can be used are all known alkanolamines which have at least one primary hydroxyl group (—CH$_2$—OH). Examples of alkanolamines which can be used as starting materials in the process according to the invention are monoaminoethanol, 3-aminopropan-1-ol, 2-aminopropan-1-ol, 4-aminobutan-1-ol, 2-aminobutan-1-ol, 3-aminobutan-1-ol, 5-aminopentan-1-ol, 2-aminopentan-1-ol, 6-aminohexan-1-ol, 2-aminohexan-1-ol, 7-aminoheptan-1-ol, 2-aminoheptan-1-ol, 8-aminooctan-1-ol, 2-aminooctan-1-ol, N-(2-hydroxyethyl)aniline, N-(2-aminoethyl)ethanolamine, 1-(2-hydroxyethyl)piperazine, 2-(2-aminoethoxy)ethanol, N-butylethanolamine, N-ethylethanolamine, N-methylethanolamine, N,N-dimethylethanolamine, N-(2-hydroxyethyl)-1,3-propanediamine, 3-(2-hydroxyethyl)amino-1-propanol, 3-dimethylamino-1-propanol, N,N-dibutylethanolamine, N,N-dimethylisopropylamine and N,N-diethylethanolamine.

Preference is given to alkanolamines which have at least one primary hydroxyl group (—CH$_2$—OH) and at least primary amino group of the formula (—CH$_2$—NH$_2$).

A particularly preferred alkanolamine is monoaminoethanol.

Complex Catalyst

The process according to the invention uses at least one complex catalyst which comprises at least one element selected from groups 8 and 9 of the Periodic Table of the Elements (nomenclature in accordance with IUPAC), and also at least one phosphorus donor ligand of the general formula (I),

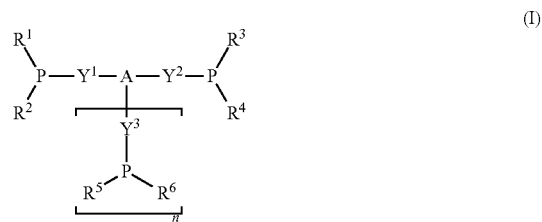

where
n is 0 or 1;
R$^1$, R$^2$, R$^3$, R$^4$, R$^5$, R$^6$ are, independently of one another, unsubstituted or at least monosubstituted C$_1$-C$_{10}$-alkyl, C$_1$-C$_4$-alkyldiphenylphosphine (—C$_1$-C$_4$-alkyl-P(phenyl)$_2$), C$_3$-C$_{10}$-cycloalkyl, C$_3$-C$_{10}$-heterocyclyl comprising at least one heteroatom selected from N, O and S, C$_5$-C$_{14}$-aryl or C$_5$-C$_{10}$-heteroaryl comprising at least one heteroatom selected from N, O and S,
where the substituents are selected from the group consisting of:
F, Cl, Br, OH, CN, NH$_2$ and C$_1$-C$_{10}$-alkyl;
A is
i) a bridging group selected from the group unsubstituted or at least monosubstituted N, O, P, C$_1$-C$_6$-alkane, C$_3$-C$_{10}$-cycloalkane, C$_3$-C$_{10}$-heterocycloalkane comprising at least one heteroatom selected from N, O and S, C$_5$-C$_{14}$-aromatic and C$_5$-C$_6$-heteroaromatic comprising at least one heteroatom selected from N, O and S, where the substituents are selected from the group consisting of:
C$_1$-C$_4$-alkyl, phenyl, F, Cl, Br, OH, OR$^7$, NH$_2$, NHR$^7$ or N(R$^7$)$_2$,
where R$^7$ is selected from C$_1$-C$_{10}$-alkyl and C$_5$-C$_{10}$-aryl;
or
ii) a bridging group of the formula (II) or (III):

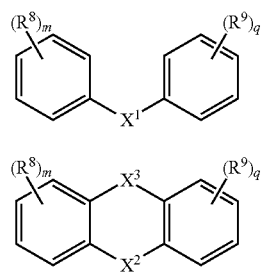

m, q are, independently of one another, 0, 1, 2, 3 or 4;
R$^8$, R$^9$ are, independently of one another, selected from the group C$_1$-C$_{10}$-alkyl, F, Cl, Br, OH, OR$^7$, NH$_2$, NHR$^7$ and N(R$^7$)$_2$,
where R$^7$ is selected from C$_1$-C$_{10}$-alkyl and C$_5$-C$_{10}$-aryl;
X$^1$, X$^2$ are, independently of one another, NH, O or S;
X$^3$ is a bond, NH, NR$^{10}$, O, S or CR$^{11}$R$^{12}$;
R$^{10}$ is unsubstituted or at least monosubstituted C$_1$-C$_{10}$-alkyl, C$_3$-C$_{10}$-cycloalkyl, C$_3$-C$_{10}$-heterocyclyl comprising at least one heteroatom selected from N, O and S, C$_5$-C$_{14}$-aryl or C$_5$-C$_{10}$-heteroaryl comprising at least one heteroatom selected from N, O and S,
where the substituents are selected from the group consisting of: F, Cl, Br, OH, CN, NH$_2$ and C$_1$-C$_{10}$-alkyl;
R$^{11}$, R$^{12}$ are, independently of one another, unsubstituted or at least monosubstituted C$_1$-C$_{10}$-alkoxy, C$_3$-C$_{10}$-cycloalkyl, C$_3$-C$_{10}$-cycloalkoxy, C$_3$-C$_{10}$-heterocyclyl comprising at least one heteroatom selected from N, O and S, C$_5$-C$_{14}$-aryl, C$_5$-C$_{14}$-aryloxy or C$_5$-C$_{10}$-heteroaryl comprising at least one heteroatom selected from N, O and S,
where the substituents are selected from the group consisting of: F, Cl, Br, OH, CN, NH$_2$ and C$_1$-C$_{10}$-alkyl;
Y$^1$, Y$^2$, Y$^3$ are, independently of one another, a bond, unsubstituted or at least monosubstituted methylene, ethylene, trimethylene, tetramethylene, pentamethylene or hexamethylene,
where the substituents are selected from the group consisting of: F, Cl, Br, OH, OR$^7$, CN, NH$_2$, NHR$^7$, N(R$^7$)$_2$ and C$_1$-C$_{10}$-alkyl,
where R$^7$ is selected from C$_1$-C$_{10}$-alkyl and C$_5$-C$_{10}$-aryl.

According to the invention, A is a bridging group. For the case that A is selected from the group unsubstituted or at least monosubstituted C$_1$-C$_6$-alkane, C$_3$-C$_{10}$-cycloalkane, C$_3$-C$_{10}$-heterocycloalkane, C$_5$-C$_{14}$-aromatic and C$_5$-C$_6$-heteroaromatic and bridging groups of the formula (II) or (III), for the case (n=0), two hydrogen atoms of the bridging group are replaced by bonds to the adjacent substituents Y$^1$ and Y$^2$. For the case (n=1), three hydrogen atoms of the bridging group are replaced by three bonds to the adjacent substituents Y$^1$, Y$^2$ and Y$^3$.

For the case that A is P (phosphorus), the phosphorus forms for the case (n=0) two bonds to the adjacent substituents Y$^1$ and Y$^2$ and one bond to a substituent selected from the group consisting of C$_1$-C$_4$-alkyl and phenyl. For the case (n=1), the phosphorus forms three bonds to the adjacent substituents Y$^1$, Y$^2$ and Y$^3$.

For the case that A is N (nitrogen), the nitrogen for the case (n=0) forms two bonds to the adjacent substituents Y$^1$ and Y$^2$ and one bond to a substituent selected from the group consisting of C$_1$-C$_4$-alkyl and phenyl. For the case (n=1), the nitrogen forms three bonds to the adjacent substituents Y$^1$, Y$^2$ and Y$^3$.

For the case that A is O (oxygen), n=0. The oxygen forms two bonds to the adjacent substituents Y$^1$ and Y$^2$.

The elements of groups 8 and 9 of the Periodic Table of the Elements comprise iron, cobalt, ruthenium, rhodium, osmium and iridium. Preference is given to complex catalysts which comprise at least one element selected from ruthenium and iridium.

In a preferred embodiment, the process according to the invention is carried out in the presence of at least one complex catalyst which comprises at least one element selected from groups 8 and 9 of the Periodic Table of the Elements, and also at least one phosphorus donor ligand of the general formula (I), where
n is 0 or 1;
R$^1$, R$^2$, R$^3$, R$^4$, R$^5$, R$^6$ are, independently of one another, unsubstituted C$_1$-C$_{10}$-alkyl, C$_3$-C$_{10}$-cycloalkyl, C$_3$-C$_{10}$-heterocyclyl comprising at least one heteroatom selected from N, O and S, C$_5$-C$_{14}$-aryl or C$_5$-C$_{10}$-heteroaryl comprising at least one heteroatom selected from N, O and S;
A is
i) a bridging group selected from the group unsubstituted C$_1$-C$_6$-alkane, C$_3$-C$_{10}$-cycloalkane, C$_3$-C$_{10}$-heterocycloalkane comprising at least one heteroatom selected from N, O and S, C$_5$-C$_{14}$-aromatic and C$_5$-C$_6$-heteroaromatic comprising at least one heteroatom selected from N, O and S;
or
ii) a bridging group of the formula (II) or (III):

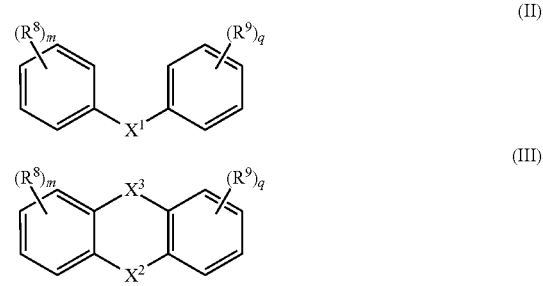

m, q are, independently of one another, 0, 1, 2, 3 or 4;
R$^8$, R$^9$ are, independently of one another, selected from the group C$_1$-C$_{10}$-alkyl, F, Cl, Br, OH, OR$^7$, NH$_2$, NHR$^7$ and N(R$^7$)$_2$,
where R$^7$ is selected from C$_1$-C$_{10}$-alkyl and C$_5$-C$_{10}$-aryl;
X$^1$, X$^2$ are, independently of one another, NH, O or S;
X$^3$ is a bond, NH, NR$^{10}$, O, S or CR$^{11}$R$^{12}$;
R$^{10}$ is unsubstituted C$_1$-C$_{10}$-alkyl, C$_3$-C$_{10}$-cycloalkyl, C$_3$-C$_{10}$-heterocyclyl comprising at least one heteroatom selected from N, O and S, $C_5$-$C_{14}$-aryl or $C_5$-$C_{10}$-heteroaryl comprising at least one heteroatom selected from N, O and S;

$R^{11}$, $R^{12}$ are, independently of one another, unsubstituted $C_1$-$C_{10}$-alkyl, $C_1$-$C_{10}$-alkoxy, $C_3$-$C_{10}$-cycloalkyl, $C_3$-$C_{10}$-cycloalkoxy, $C_3$-$C_{10}$-heterocyclyl comprising at least one heteroatom selected from N, O and S, $C_5$-$C_{14}$-aryl, $C_5$-$C_{14}$-aryloxy or $C_5$-$C_{10}$-heteroaryl comprising at least one heteroatom selected from N, O and S;

$Y^1$, $Y^2$, $Y^3$ are, independently of one another, a bond, unsubstituted methylene, ethylene, trimethylene, tetramethylene, pentamethylene or hexamethylene.

In a further preferred embodiment, the process according to the invention is carried out in the presence of at least one complex catalyst which comprises at least one element selected from groups 8 and 9 of the Periodic Table of the Elements, and also at least one phosphorus donor ligand of the general formula (V),

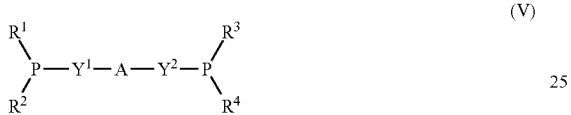

(V)

where $R^1$, $R^2$, $R^3$, $R^4$ are, independently of one another, unsubstituted or at least monosubstituted $C_1$-$C_{10}$-alkyl, $C_1$-$C_4$-alkyldiphenylphosphine (—$C_1$-$C_4$-alkyl-P(phenyl)$_2$), $C_3$-$C_{10}$-cycloalkyl, $C_3$-$C_{10}$-heterocyclyl comprising at least one heteroatom selected from N, O and S, $C_5$-$C_{14}$-aryl or $C_5$-$C_{10}$-heteroaryl comprising at least one heteroatom selected from N, O and S, where the substituents are selected from the group consisting of: F, Cl, Br, OH, CN, $NH_2$ and $C_1$-$C_{10}$-alkyl;

A is i) a bridging group selected from the group unsubstituted or at least monosubstituted N, O, P, $C_1$-$C_6$-alkane, $C_3$-$C_{10}$-cycloalkane, $C_3$-$C_{10}$-heterocycloalkane comprising at least one heteroatom selected from N, O and S, $C_5$-$C_{14}$-aromatic and $C_5$-$C_6$-heteroaromatic comprising at least one heteroatom selected from N, O and S, where the substituents are selected from the group consisting of:

$C_1$-$C_4$-alkyl, phenyl, F, Cl, Br, OH, $OR^7$, $NH_2$, $NHR^7$ or $N(R^7)_2$;

where $R^7$ is selected from $C_1$-$C_{10}$-alkyl and $C_5$-$C_{10}$-aryl; or ii) a bridging group of the formula II or III:

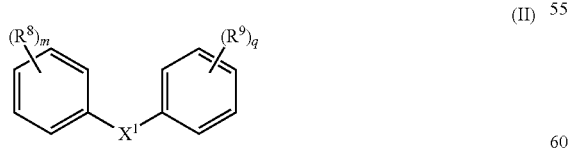

(II)

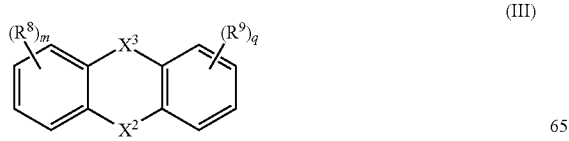

(III)

m, q are, independently of one another, 0, 1, 2, 3 or 4;

$R^8$, $R^9$ are, independently of one another, selected from the group $C_1$-$C_{10}$-alkyl, F, Cl, Br, OH, $OR^7$, $NH_2$, $NHR^7$ and $N(R^7)_2$, where $R^7$ is selected from $C_1$-$C_{10}$-alkyl and $C_5$-$C_{10}$-aryl;

$X^1$, $X^2$ are, independently of one another, NH, O or S;

$X^3$ is a bond, NH, $NR^{10}$, O, S or $CR^{11}R^{12}$;

$R^{10}$ is unsubstituted or at least monosubstituted $C_1$-$C_{10}$-alkyl, $C_3$-$C_{10}$-cycloalkyl, $C_3$-$C_{10}$-heterocyclyl comprising at least one heteroatom selected from N, O and S, $C_5$-$C_{14}$-aryl or $C_5$-$C_{10}$-heteroaryl comprising at least one heteroatom selected from N, O and S, where the substituents are selected from the group consisting of: F, Cl, Br, OH, CN, $NH_2$ and $C_1$-$C_{10}$-alkyl;

$R^{11}$, $R^{12}$ are, independently of one another, unsubstituted or at least monosubstituted $C_1$-$C_{10}$-alkoxy, $C_3$-$C_{10}$-cycloalkyl, $C_3$-$C_{10}$-cycloalkoxy, $C_3$-$C_{10}$-heterocyclyl comprising at least one heteroatom selected from N, O and S, $C_5$-$C_{14}$-aryl, $C_5$-$C_{14}$-aryloxy or $C_5$-$C_{10}$-heteroaryl comprising at least one heteroatom selected from N, O and S, where the substituents are selected from the group consisting of: F, Cl, Br, OH, CN, $NH_2$ and $C_1$-$C_{10}$-alkyl;

$Y^1$, $Y^2$ are, independently of one another, a bond, unsubstituted or at least monosubstituted methylene, ethylene, trimethylene, tetramethylene, pentamethylene or hexamethylene, where the substituents are selected from the group consisting of: F, Cl, Br, OH, $OR^7$, CN, $NH_2$, $NHR^7$, $N(R^7)_2$ and $C_1$-$C_{10}$-alkyl, where $R^7$ is selected from $C_1$-$C_{10}$-alkyl and $C_5$-$C_{10}$-aryl.

In a further preferred embodiment, the process according to the invention is carried out in the presence of at least one complex catalyst which comprises at least one element selected from groups 8 and 9 of the Periodic Table of the Elements, and also at least one phosphorus donor ligand of the general formula (VI),

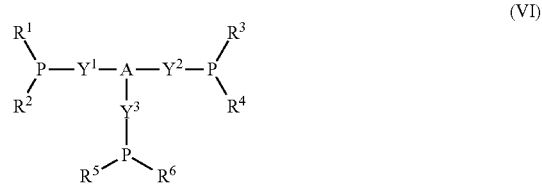

(VI)

where $R^1$, $R^2$, $R^3$, $R^4$, $R^5$, $R^6$ are, independently of one another, unsubstituted or at least monosubstituted $C_1$-$C_{10}$-alkyl, $C_1$-$C_4$-alkyldiphenylphosphine, $C_3$-$C_{10}$-cycloalkyl, $C_3$-$C_{10}$-heterocyclyl comprising at least one heteroatom selected from N, O and S, $C_5$-$C_{14}$-aryl or $C_5$-$C_{10}$-heteroaryl comprising at least one heteroatom selected from N, O and S, where the substituents are selected from the group consisting of: F, Cl, Br, OH, CN, $NH_2$ and $C_1$-$C_{10}$-alkyl;

A is a bridging group selected from the group unsubstituted or at least monosubstituted N, P, $C_1$-$C_6$-alkane, $C_3$-$C_{10}$-cycloalkane, $C_3$-$C_{10}$-heterocycloalkane comprising at least one heteroatom selected from N, O and S, $C_5$-$C_{14}$-aromatic and $C_5$-$C_6$-heteroaromatic comprising at least one heteroatom selected from N, O and S, where the substituents are selected from the group consisting of:

$C_1$-$C_4$-alkyl, phenyl, F, Cl, Br, OH, $OR^7$, $NH_2$, $NHR^7$ or $N(R^7)_2$, where $R^7$ is selected from $C_1$-$C_{10}$-alkyl and $C_5$-$C_{10}$-aryl;

$Y^1$, $Y^2$, $Y^3$ are, independently of one another, a bond, unsubstituted or at least monosubstituted methylene, ethylene, trimethylene, tetramethylene, pentamethylene or hexamethylene, where the substituents are selected from the group consisting of: F, Cl, Br, OH, $OR^7$, CN, $NH_2$, $NHR^7$, $N(R^7)_2$ and $C_1$-$C_{10}$-alkyl, where $R^7$ is selected from $C_1$-$C_{10}$-alkyl and $C_5$-$C_{10}$-aryl.

In a further preferred embodiment, the process according to the invention is carried out in the presence of at least one complex catalyst which comprises at least one element selected from groups 8 and 9 of the Periodic Table of the Elements, and at least one phosphorus donor ligand of the general formula (V), where $R^1$, $R^2$, $R^3$, $R^4$ are, independently of one another, methyl, ethyl, isopropyl, tert-butyl, cyclopentyl, cyclohexyl, phenyl or mesityl;

A is i) a bridging group selected from the group methane, ethane, propane, butane, cyclohexane, benzene, napthalene and anthracene;

or ii) a bridging group of the formula (VII) or (VIII):

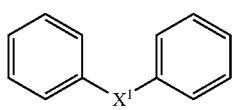

(VII)

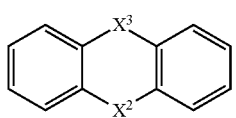

(VIII)

$X^1$, $X^2$ are, independently of one another, NH, O or S;

$X^3$ is a bond, NH, O, S or $CR^{11}R^{12}$;

$R^{11}$, $R^{12}$ are, independently of one another, unsubstituted $C_1$-$C_{10}$-alkyl;

$Y^1$, $Y^2$ are, independently of one another, a bond, methylene or ethylene.

In a particularly preferred embodiment, the process according to the invention is carried out in the presence of at least one complex catalyst which comprises at least one element selected from groups 8 and 9 of the Periodic Table of the Elements, and also at least one phosphorus donor ligand of the general formula (IX) or (X),

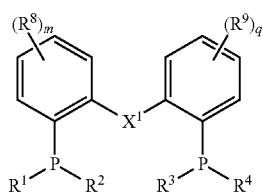

(IX)

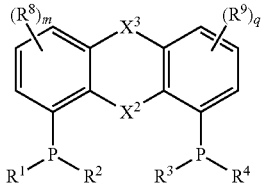

(X)

where for m, q, $R^1$, $R^2$, $R^3$, $R^4$, $R^8$, $R^9$, $X^1$, $X^2$ and $X^3$, the definitions and preferences listed above are applicable.

In a further particularly preferred embodiment, the process according to the invention is carried out in the presence of at least one complex catalyst which comprises at least one element selected from the group ruthenium and iridium, and also at least one phosphorus donor ligand selected from the group 1,2-bis(diphenylphosphino)ethane (dppe), 1,2-bis(dicylohexylphosphino)ethane, 1,3-bis(diphenylphosphino)propane (dppp), 1,4-bis(diphenylphosphino)butane (dppb), 2,3-bis(dicyclohexylphosphino)ethane (dcpe), 4,5-bis(diphenylphosphino)-9,9-dimethylxanthene (xantphos), 1,1'-[2,7-bis(1,1-dimethylethyl)-9,9-dimethyl-9H-xanthene-4,5-diyl]bis[1,1-diphenyl]phosphin (t-bu-xantphos), bis(2-diphenylphosphinoethyl)phenylphosphine and 1,1,1-tris(diphenylphosphinomethyl)ethane (triphos). Further preferred is the phosphorous donor ligand t-bu-xanthphos.

In a further particularly preferred embodiment, the process according to the invention is carried out in the presence of a complex catalyst which comprises ruthenium, and also at least one phosphorus donor ligand selected from the group 4,5-bis(diphenylphosphino)-9,9-dimethylxanthene (xantphos), bis(2-diphenylphosphinoethyl)phenylphosphine and 1,1,1-tris(diphenylphosphinomethyl)ethane (triphos).

In a further particularly preferred embodiment, the process according to the invention is carried out in the presence of a complex catalyst which comprises iridium, and also at least one phosphorus donor ligand selected from the group 4,5-bis(diphenylphosphino)-9,9-dimethylxanthene (xantphos), bis(2-diphenylphosphinoethyl)phenylphosphine and 1,1,1-tris(diphenylphosphinomethyl)ethane (triphos).

Within the context of the present invention, $C_1$-$C_{10}$-alkyl are understood as meaning branched, unbranched, saturated and unsaturated groups. Preference is given to alkyl groups having 1 to 6 carbon atoms ($C_1$-$C_6$-alkyl). More preference is given to alkyl groups having 1 to 4 carbon atoms ($C_1$-$C_4$-alkyl).

Examples of saturated alkyl groups are methyl, ethyl, n-propyl, isopropyl, n-butyl, isobutyl, sec-butyl, tert-butyl, amyl and hexyl.

Examples of unsaturated alkyl groups (alkenyl, alkynyl) are vinyl, allyl, butenyl, ethynyl and propynyl.

The $C_1$-$C_{10}$-alkyl group can be unsubstituted or substituted with one or more substituents selected from the group F, Cl, Br, hydroxy (OH), $C_1$-$C_{10}$-alkoxy, $C_5$-$C_{10}$-aryloxy, $C_5$-$C_{10}$-alkylaryloxy, $C_5$-$C_{10}$-heteroaryloxy comprising at least one heteroatom selected from N, O, S, oxo, $C_3$-$C_{10}$-cycloalkyl, phenyl, $C_5$-$C_{10}$-heteroaryl comprising at least one heteroatom selected from N, O, S, $C_5$-$C_{10}$-heterocyclyl comprising at least one heteroatom selected from N, O, S, naphthyl, amino, $C_1$-$C_{10}$-alkylamino, $C_5$-$C_{10}$-arylamino, $C_5$-$C_{10}$-heteroarylamino comprising at least one heteroatom selected from N, O, S, $C_1$-$C_{10}$-dialkylamino, $C_{10}$-$C_{12}$-diarylamino, $C_{10}$-$C_{20}$-alkylarylamino, $C_1$-$C_{10}$-acyl, $C_1$-$C_{10}$-acyloxy, $NO_2$, $C_1$-$C_{10}$-carboxy, carbamoyl, carboxamide, cyano, sulfonyl, sulfonylamino, sulfinyl, sulfinylamino, thiol, $C_1$-$C_{10}$-alkylthiol, $C_5$-$C_{10}$-arylthiol or $C_1$-$C_{10}$-alkylsulfonyl.

The above definition for $C_1$-$C_{10}$-alkyl applies accordingly to $C_1$-$C_{30}$-alkyl and to $C_1$-$C_6$-alkane.

In the present case, $C_3$-$C_{10}$-cycloalkyl is understood as meaning saturated, unsaturated monocyclic and polycyclic groups. Examples of $C_3$-$C_{10}$-cycloalkyl are cyclopropyl, cyclobutyl, cyclopentyl, cyclohexyl or cycloheptyl. The cycloalkyl groups can be unsubstituted or substituted with one or more substituents, as has been defined above in relation to the group $C_1$-$C_{10}$-alkyl.

The definition of $C_3$-$C_{10}$-cycloalkyl specified above applies accordingly to $C_3$-$C_{10}$-cycloalkane.

Within the context of the present invention, $C_5$-$C_{14}$-aryl is understood as meaning an aromatic ring system having 5 to 14 carbon atoms. The aromatic ring system can be monocyclic or bicyclic. Examples of aryl groups are phenyl, naphthyl, such as 1-naphthyl and 2-naphthyl. The aryl group can be unsubstituted or substituted with one or more substituents as defined above under $C_1$-$C_{10}$-alkyl.

The definition of $C_5$-$C_{14}$-aryl given above applies accordingly to $C_5$-$C_{14}$-aromatic.

Within the context of the present invention, $C_5$-$C_{10}$-heteroaryl is understood as meaning a heteroaromatic system which comprises at least one heteroatom selected from the group N, O and S. The heteroaryl groups can be monocyclic or bicyclic. For the case that nitrogen is a ring atom, the present invention also comprises N-oxides of the nitrogen-comprising heteroaryls. Examples of heteroaryls are thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolinyl, quinolinyl, acridinyl, naphthyridinyl, quinoxalinyl, quinazolinyl, cinnolinyl, piperidinyl, carbolinyl, thiazolyl, oxazolyl, isothiazolyl, isoxazolyl. The heteroaryl groups can be unsubstituted or substituted with one or more substituents which have been defined above under $C_1$-$C_{10}$-alkyl.

The definition for $C_5$-$C_{10}$-heteroaryl given above applies accordingly to $C_5$-$C_6$-heteroaromatic.

Within the context of the present invention, $C_3$-$C_{10}$-heterocyclyl is understood as meaning five- to ten-membered ring systems which comprise at least one heteroatom from the group N, O and S. The ring systems can be monocyclic or bicyclic. Examples of suitable heterocyclic ring systems are piperidinyl, pyrrolidinyl, pyrrolinyl, pyrazolinyl, pyrazolidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl and tetrahydropyranyl.

The definition of $C_3$-$C_{10}$-heterocyclyl given above applies accordingly to $C_3$-$C_{10}$-heterocycloalkane.

Alcohol Amination

The homogeneous catalysts can either be generated directly in their active form, or else are only generated under the reaction conditions starting from customary precursors with the addition of the corresponding ligands. Customary precursors are, for example, [Ru(p-cymene)Cl$_2$]$_2$, [Ru(benzene)Cl$_2$]$_n$, [Ru(CO)$_2$Cl$_2$]$_n$, [Ru(CO)$_3$Cl$_2$]$_2$, [Ru(COD)(allyl)], [RuCl$_3$*H$_2$O], [Ru(acetylacetonate)$_3$], [Ru(DMSO)$_4$Cl$_2$], [Ru(PPh$_3$)$_3$(CO)(H)Cl], [Ru(PPh$_3$)$_3$(CO)Cl$_2$], [Ru(PPh$_3$)$_3$(CO)(H)$_2$], [Ru(PPh$_3$)$_3$Cl$_2$], [Ru(cyclopentadienyl)(PPh$_3$)$_2$Cl], [Ru(cyclopentadienyl)(CO)$_2$Cl], [Ru(cyclopentadienyl)(CO)$_2$H], [Ru(cyclopentadienyl)(CO)$_2$]$_2$, [Ru(pentamethylcyclopentadienyl)(CO)$_2$Cl], [Ru(pentamethylcylcopentadienyl)(CO)$_2$H], [Ru(pentamethylcyclopentadienyl)(CO)$_2$]$_2$, [Ru(indenyl)(CO)$_2$Cl], [Ru(indenyl)(CO)$_2$H], [Ru(indenyl)(CO)$_2$]$_2$, ruthenocene, [Ru(binap)Cl$_2$], [Ru(bipyridine)$_2$Cl$_2$*2H$_2$O], [Ru(COD)Cl$_2$]$_2$, [Ru(pentamethylcyclopentadienyl)(COD)Cl], [Ru$_3$(CO)$_{12}$], [Ru(tetraphenylhydroxycyclopentadienyl)(CO)$_2$H], [Ru(PMe$_3$)$_4$(H)$_2$], [Ru(PEt$_3$)$_4$(H)$_2$], [Ru(PnPr$_3$)$_4$(H)$_2$], [Ru(PnBu$_3$)$_4$(H)$_2$], [Ru(Pnoctyl$_3$)$_4$(H)$_2$], [IrCl$_3$*H$_2$O], KIrCl$_4$, K$_3$IrCl$_6$, [Ir(COD)Cl]$_2$, [Ir(cyclooctene)$_2$Cl]$_2$, [Ir(ethene)$_2$Cl]$_2$, [Ir(cyclopentadienyl)Cl$_2$]$_2$, [Ir(pentamethylcyclopentadienyl)Cl$_2$]$_2$, [Ir(cyclopentadienyl)(CO)$_2$], [Ir(pentamethylcyclopentadienyl)(CO)$_2$], [Ir(PPh$_3$)$_2$(CO)(H)], [Ir(PPh$_3$)$_2$(CO)(Cl)], [Ir(PPh$_3$)$_3$(Cl)].

Within the context of the present invention, homogeneously catalyzed is understood as meaning that the catalytically active part of the complex catalyst is present in at least partially dissolved form in the liquid reaction medium. In a preferred embodiment, at least 90% of the complex catalyst used in the process is present in dissolved form in the liquid reaction medium, more preferably at least 95%, especially preferably more than 99%, most preferably the complex catalyst is present in completely dissolved form in the liquid reaction medium (100%), in each case based on the total amount in the liquid reaction medium.

The amount of metal component in the catalyst, preferably ruthenium or iridium, is generally 0.1 to 5000 ppm by weight, in each case based on the total liquid reaction medium.

The reaction takes place in the liquid phase generally at a temperature of from 20 to 250° C. Preferably, the process according to the invention is carried out at temperatures in the range from 100° C. to 200° C., particularly preferably in the range from 110 to 160° C.

The reaction can generally be carried out at a total pressure of from 0.1 to 20 MPa absolute, which can either be the intrinsic pressure of the solvent at the reaction temperature, or else the pressure of a gas such as nitrogen, argon or hydrogen. Preferably, the process according to the invention is carried out at a total pressure in the range from 0.5 to 15 MPa absolute, particularly preferably at a total pressure in the range from 1 to 10 MPa absolute.

The average reaction time is generally 15 minutes to 100 hours.

The aminating agent (ammonia) can be used in stoichiometric, substoichiometric or superstoichiometric amounts with regard to the hydroxyl groups to be aminated.

In a preferred embodiment, ammonia is used in a 1.5- to 250-fold, preferably in a 2- to 100-fold, in particular in a 2- to 10-fold, molar excess per mole of hydroxyl groups to be reacted in the starting material. Even higher excesses of ammonia are possible.

The process according to the invention can be carried out either in a solvent or else without solvents. Suitable solvents are polar and nonpolar solvents which can be used in pure form or in mixtures. For example, only one nonpolar or one polar solvent can be used in the process according to the invention. It is also possible to use mixtures of two or more polar solvents or mixtures of two or more nonpolar solvents or mixtures of one or more polar solvents with one or more nonpolar solvents. The product can also be used as solvent in pure form or in mixtures with polar or nonpolar solvents.

Suitable nonpolar solvents are, for example, saturated and unsaturated hydrocarbons such as hexane, heptane, octane, cyclohexane, benzene, toluene, xylene and mesitylene, and linear and cyclic ethers such as THF, diethyl ether, 1,4-dioxane, MTBE (tert-butyl methyl ether), diglyme and 1,2-dimethoxyethane. Preference is given to using toluene, xylenes or mesitylene. Depending on the polarity of the product, the product can also be used as nonpolar solvent for the reaction.

Suitable polar solvents are, for example, water, dimethylformamide, formamide, tert-amylalcohol and acetonitrile. Preference is given to using water. The water can either be added before the reaction, be formed during the reaction as water of reaction, or else be added after the reaction in addition to the water of reaction. Depending on the polarity of the product, the product can also be used as polar solvent for the reaction. A further preferred solvent is tert-amylalcohol.

For the reaction in the liquid phase, ammonia, the starting material having at least one functional group of the formula (—$CH_2$—OH), optionally together with one or more solvents, are introduced into a reactor together with the complex catalyst.

The introduction of ammonia, starting material, optionally solvent and complex catalyst can take place here simultaneously or separately from one another. The reaction can be carried out continuously, in semibatch procedure, in batch procedure, back-mixed in product as solvent or not back-mixed in a straight run.

For the process according to the invention, all reactors can in principle be used which are fundamentally suitable for gas/liquid reactions under the stated temperature and the stated pressure. Suitable standard reactors for gas/liquid and for liquid/liquid reaction systems are discussed, for example, in K. D. Henkel, "Reactor Types and Their Industrial Applications", in Ullmann's Encyclopedia of Industrial Chemistry, 2005, Wiley-VCH Verlag GmbH & Co. KGaA, DOI: 10.1002/14356007.b04_087, Chapter 3.3 "Reactors for gas-liquid reactions". Examples which may be mentioned are stirred-tank reactors, tubular reactors or bubble column reactors.

During the amination reaction, at least one primary hydroxyl group (—$CH_2$—OH) of the starting material is reacted with ammonia to give a primary amino group (—$CH_2$—$NH_2$), where, in each case, one mol of water of reaction is formed per mole of reacted hydroxyl group.

Thus, during the reaction of alkanolamines which have only one primary hydroxyl group (—$CH_2$—OH), the corresponding diamines are formed. The reaction of monoaminoethanol thus leads to the corresponding 1,2-diaminoethane.

During the reaction of starting materials which, besides the functional group of the formula (—$CH_2$—OH), have a further hydroxyl group (diols), preferably only the primary alcohol group (—$CH_2$—OH) is aminated. The reaction of 1,2-ethylene glycol thus leads to the corresponding monoethanolamine. It is also possible to aminate both hydroxyl groups to give 1,2-diaminoethane.

In the case of the reaction of starting materials which, besides the functional group of the formula (—$CH_2$—OH), have two further hydroxyl groups (triols), preferably only one primary alcohol group (—$CH_2$—OH) is aminated. It is also possible to react two or three hydroxyl groups with ammonia to give the corresponding primary diamines or triamines. The formation of primary monoamines, diamines or triamines can be controlled here via the amount of ammonia used and via the reaction conditions.

In the case of the reaction of starting materials which, besides the functional group of the formula (—$CH_2$—OH), have more than three further hydroxyl groups (polyols), preferably only one primary alcohol group (—$CH_2$—OH) is aminated. It is also possible to react two, three or more hydroxyl groups with ammonia to give the corresponding primary monoamines, diamines, triamines or polyamines. The formation of the primary monoamines, diamines, triamines and polyamines can be controlled here via the amount of ammonia used and via the reaction conditions.

The reaction product which is formed during the reaction generally comprises the corresponding amination products, optionally the one or more solvents, the complex catalyst, any unreacted starting materials and ammonia, and also the water of reaction that is formed.

Any excess ammonia present, the optionally present solvents, the complex catalyst and the water of reaction are removed from the reaction product. The amination product obtained can be worked-up further. The excess ammonia, the complex catalyst, optionally the solvent or solvents and any unreacted starting materials can be returned to the amination reaction.

If the amination reaction is carried out without solvents, then the homogeneous complex catalyst is dissolved in the product after the reaction. This can remain in the product or be separated off from it by means of a suitable method. Possibilities for separating off the catalyst are, for example, washing with a product-immiscible solvent in which the catalyst dissolves better through appropriate choice of the ligands than in the product. Optionally, the concentration of the catalyst is reduced by means of multistage extraction from the product. The extractant used is preferably a solvent also suitable for the target reaction, such as toluene, benzene, xylenes, alkanes, such as hexanes, heptanes and octanes, and acyclic or cyclic ethers, such as diethyl ether and tetrahydrofuran, which, following concentration by evaporation, can be used again for the reaction together with the extracted catalyst. It is also possible to remove the catalyst with a suitable absorber material. Removal can also take place by adding water to the product phase if the reaction is carried out in a water-immiscible solvent. If the catalyst here dissolves preferentially in the solvent, it can be separated off with the solvent from the aqueous product phase and optionally be re-used. This can be brought about by choosing suitable ligands. The resulting aqueous mono-, di-, tri- or polyamines can be used directly as technical-grade amine solutions. It is also possible to separate the amination product from the catalyst by distillation.

If the reaction is carried out in a solvent, then this may be miscible with the amination product and can be separated off by distillation after the reaction. It is also possible to use solvents which have a miscibility gap with the amination products or the starting materials. Suitable solvents for this purpose which may be mentioned are, for example, toluene, benzene, xylenes, alkanes, such as hexanes, heptanes and octanes, and acyclic or cyclic ethers, such as diethyl ether, tetrahydrofuran and dioxane. Through appropriate choice of the phosphine ligands, the catalyst preferentially dissolves in the solvent phase, i.e. in the non-product-comprising phase. The phosphine ligands can also be selected such that the catalyst dissolves in the amination product. In this case, the amination product can be separated from the catalyst by distillation.

The solvent can also be miscible with the starting materials and the product under the reaction conditions and only form a second liquid phase which comprises the majority of the catalyst after cooling. Solvents which exhibit this property which may be mentioned are, for example, toluene, benzene, xylenes, alkanes, such as hexanes, heptanes and octanes. The catalyst can then be separated off together with the solvent and be re-used. The product phase can also be admixed with water in this variant. The fraction of the catalyst comprised in the product can then be separated off by means of suitable absorber materials such as, for example, polyacrylic acid and salts thereof, sulfonated polystyrenes and salts thereof, active carbons, montmorillonites, bentonites and also zeolites, or else be left in the product.

The amination reaction can also be carried out in two phases. For the embodiment of the two-phase reaction procedure, suitable nonpolar solvents are in particular toluene, benzene, xylenes, alkanes, such as hexanes, heptanes and octanes, in combination with lipophilic phosphine ligands on the transition metal catalyst, as a result of which the transition metal catalyst accumulates in the nonpolar phase. In this embodiment, in which the product and also the water of reaction and optionally unreacted starting materials form a second phase enriched with these compounds, the majority of the catalyst can be separated off from the product phase by simple phase separation and be re-used.

If volatile by-products or unreacted starting materials or else the water formed during the reaction or added after the reaction to improve extraction are undesired, these can be separated off from the product without problems by distillation.

It can also be advantageous to continuously remove the water formed during the reaction from the reaction mixture. The water of reaction can be separated off directly by distillation from the reaction mixture or as azeotrope with the addition of a suitable solvent (entrainer) and using a water separator, or can be removed by adding water-removing auxiliaries.

The addition of bases can have a positive effect on the product formation. Suitable bases which may be mentioned here are alkali metal hydroxides, alkaline earth metal hydroxides, alkali metal alcoholates, alkaline earth metal alcoholates, alkali metal carbonates and alkaline earth metal carbonates, of which 0.01 to 100 molar equivalents, based on the metal catalyst used, can be used.

The present invention further provides for the use of a complex catalyst which comprises at least one element selected from groups 8 and 9 of the Periodic Table of the Elements, and also at least one phosphorus donor ligand of the general formula (I),

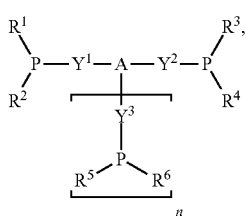
(I)

where
n is 0 or 1;
$R^1$, $R^2$, $R^3$, $R^4$, $R^5$, $R^6$ are, independently of one another, unsubstituted or at least monosubstituted $C_1$-$C_{10}$-alkyl, $C_1$-$C_4$-alkyldiphenylphosphine (—$C_1$-$C_4$-alkyl-P(phenyl)$_2$), $C_3$-$C_{10}$-cycloalkyl, $C_3$-$C_{10}$-heterocyclyl comprising at least one heteroatom selected from N, O and S, $C_5$-$C_{14}$-aryl or $C_5$-$C_{10}$-heteroaryl comprising at least one heteroatom selected from N, O and S,
where the substituents are selected from the group consisting of:
F, Cl, Br, OH, CN, $NH_2$ and $C_1$-$C_{10}$-alkyl;
A is
i) a bridging group selected from the group unsubstituted or at least monosubstituted N, O, P, $C_1$-$C_6$-alkane, $C_3$-$C_{10}$-cycloalkane, $C_3$-$C_{10}$-heterocycloalkane comprising at least one heteroatom selected from N, O and S, $C_5$-$C_{14}$-aromatic or $C_5$-$C_6$-heteroaromatic comprising at least one heteroatom selected from N, O and S,
where the substituents are selected from the group consisting of:
$C_1$-$C_4$-alkyl, phenyl, F, Cl, Br, OH, $OR^7$, $NH_2$, $NHR^7$ or $N(R^7)_2$,
where $R^7$ is selected from $C_1$-$C_{10}$-alkyl and $C_5$-$C_{10}$-aryl;
or
ii) a bridging group of the formula (II) or (III):

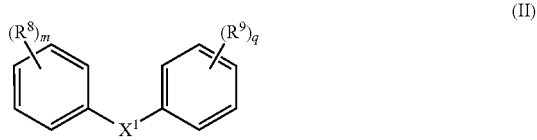
(II)

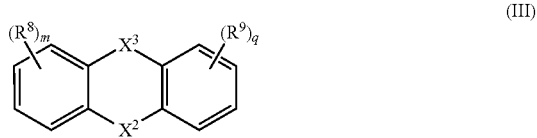
(III)

m, q are, independently of one another, 0, 1, 2, 3 or 4;
$R^8$, $R^9$ are, independently of one another, selected from the group $C_1$-$C_{10}$-alkyl, F, Cl, Br, OH, $OR^7$, $NH_2$, $NHR^7$ and $N(R^7)_2$,
where $R^7$ is selected from $C_1$-$C_{10}$-alkyl and $C_5$-$C_{10}$-aryl;
$X^1$, $X^2$ are, independently of one another, NH, O or S;
$X^3$ is a bond, NH, $NR^{10}$, O, S or $CR^{11}R^{12}$;
$R^{10}$ is unsubstituted or at least monosubstituted $C_1$-$C_{10}$-alkyl, $C_3$-$C_{10}$-cycloalkyl, $C_3$-$C_{10}$-heterocyclyl comprising at least one heteroatom selected from N, O and S, $C_5$-$C_{14}$-aryl or $C_5$-$C_{10}$-heteroaryl comprising at least one heteroatom selected from N, O and S,
where the substituents are selected from the group consisting of: F, Cl, Br, OH, CN, $NH_2$ and $C_1$-$C_{10}$-alkyl;
$R^{11}$, $R^{12}$ are, independently of one another, unsubstituted or at least monosubstituted $C_1$-$C_{10}$-alkyl, $C_1$-$C_{10}$-alkoxy, $C_3$-$C_{10}$-cycloalkyl, $C_3$-$C_{10}$-cycloalkoxy, $C_3$-$C_{10}$-heterocyclyl comprising at least one heteroatom selected from N, O and S, $C_5$-$C_{14}$-aryl, $C_5$-$C_{14}$-aryloxy or $C_5$-$C_{10}$-heteroaryl comprising at least one heteroatom selected from N, O and S,
where the substituents are selected from the group consisting of: F, Cl, Br, OH, CN, $NH_2$ and $C_1$-$C_{10}$-alkyl;
$Y^1$, $Y^2$, $Y^3$ are, independently of one another, a bond, unsubstituted or at least monosubstituted methylene, ethylene, trimethylene, tetramethylene, pentamethylene or hexamethylene,
where the substituents are selected from the group consisting of: F, Cl, Br, OH, $OR^7$, CN, $NH_2$, $NHR^7$, $N(R^7)_2$ and $C_1$-$C_{10}$-alkyl,
where $R^7$ is selected from $C_1$-$C_{10}$-alkyl and $C_5$-$C_{10}$-aryl,
for the homogeneously catalyzed preparation of primary amines which have at least one functional group of the formula (—$CH_2$—$NH_2$), by alcohol amination of starting materials which have at least one functional group of the formula (—$CH_2$—OH) with ammonia.

For the use of the complex catalyst for the homogeneously catalyzed preparation of primary amines which have at least one functional group of the formula (—$CH_2$—$NH_2$) by alcohol amination of starting materials which have at least one functional group of the formula (—$CH_2$—OH) with ammonia, the definitions and preferences described for the process according to the invention are applicable.

The invention is illustrated by the examples below without limiting it thereto.

EXAMPLES

General procedure for the catalytic amination according to the invention of alcohols with ammonia:

Ligand L, metal salt M, solvent and the stated alcohol were introduced as initial charge under an Ar atmosphere in a 160 ml Parr autoclave (hte, (stainless steel V4A)) with magnetically coupled slanted-blade stirrer (stirring speed: 200-500 revolutions/minute). The stated amount of ammonia was either precondensed at room temperature or directly metered in from the $NH_3$ pressurized-gas bottle. If hydrogen was used, this was carried out by means of iterative differential pressure metering. The steel autoclave was heated electrically up to the stated temperature and heated (internal temperature measurement) for the stated time with stirring (500 revolutions/minute). After cooling to room temperature, decompressing the autoclave and outgassing the ammonia at atmospheric pressure, the reaction mixture was analyzed by means of GC (30 m RTX5 amine 0.32 mm 1.5 μm). Purification of the particular product can be carried out, for example, by distillation. The results for the amination of octanol (Table 1a and 1b), 1,4-butanediol (Table 2), diethylene glycol (Table 3), 1,9-nonanediol, 1,6-hexanediol, 1,10-decandiol (Table 4) and 1,2-dimethanolfuran (Table 5) are given below:

| Ligand name (L) | CAS | IUPAC |
| --- | --- | --- |
| Triphos | 22031-12-5 | 1,1,1-Tris(diphenylphosphinomethyl)ethane |
| Xantphos | 161265-03-8 | 4,5-Bis(diphenylphosphino)-9,9-dimethylxanthene |
| S-Phos | 657408-07-6 | 2-Dicyclohexylphosphino-2',6'-dimethoxybiphenyl |
| Rhodaphos | n.a. | 1,1,1-Tris(diethylphosphinomethyl)ethane |
| DPPEPP | 23582-02-7 | Bis(2-diphenylphosphinoethyl)phenylphosphine |
| Tetraphos | 23582-03-8 | Tris[2-(diphenylphosphino)ethyl]phosphine |
| tBu-Xantphos | 221462-97-1 | 1,1'-[2,7-bis(1,1-dimethylethyl)-9,9-dimethyl-9H-xanthene-4,5-diyl]bis[1,1-diphenyl]phosphine |
| tBuPPyP | 338800-13-8 | 2,6-Bis[(di-tert-butylphosphino)methyl]pyridine |
| DPEPhos | 166330-10-5 | Bis[2-(diphenylphosphanyl)phenyl]ether |
| Depe | 6411-21-8 | 1,2-Bis(diethylphosphino)ethane |

TABLE 1a $$\text{\textasciitilde\textasciitilde\textasciitilde OH} \xrightarrow[-H_2O]{NH_3} \text{\textasciitilde\textasciitilde\textasciitilde NH}_2$$

| No.[a] | Solvent | T [°C.] | $NH_3$ [Eq.][f] | Reaction pressure [bar] | Metal salt [M] | Met. [M] (mol %) | Ligand [L] | Lig. [L] (mol %) | Conversion[b] | Selectivity[c] |
| --- | --- | --- | --- | --- | --- | --- | --- | --- | --- | --- |
| 1 | p-Xylene | 155 | 6 | 42 | [RuHCl(CO)(PPh$_3$)$_3$] | 0.10 | | | 6.1 | 1.4 |
| 2 | p-Xylene | 155 | 6 | 41 | [RuHCl(CO)(PPh$_3$)$_3$] | 0.10 | Triphos | 0.10 | 58.6 | 83.6 |
| 3 | Toluene | 180 | 6 | 40 | [RuHCl(CO)(PPh$_3$)$_3$] | 0.20 | Triphos | 0.20 | 99.1 | 91.8 |
| 5 | p-Xylene | 155 | 6 | 43 | [Ru(COD)methylallyl$_2$] | 0.10 | Tetraphos | 0.10 | 13.1 | 21.4 |
| 6 | p-Xylene | 155 | 6 | 43 | [RuHCl(CO)(PPh$_3$)$_3$] | 0.10 | Xantphos | 0.10 | 29.8 | 77.1 |
| 7 | p-Xylene | 155 | 6 | 42 | [RuHCl(CO)(PPh$_3$)$_3$] | 0.10 | Triphenylphosphine | 0.30 | 6.4 | 0.4 |
| 8 | p-Xylene | 155 | 6 | 41 | [Ru(COD)methylallyl$_2$] | 0.10 | Sphos | 0.10 | 3.5 | 21.7 |
| 9 | Toluene | 155 | 6 | 42 | [RuHCl(CO)(PPh$_3$)$_3$] | 0.10 | DPPEPP | 0.10 | 46.9 | 74.4 |
| 10 | Toluene | 155 | 6 | 44 | [RuHCl(CO)(PPh$_3$)$_3$] | 0.10 | Rhodaphos | 0.10 | 24.0 | 44.8 |
| 11[d] | p-Xylene | 160 | 6 | n.d. | [Ru(COD)methylallyl$_2$] | 0.20 | DPEPhos | 0.20 | 14.7 | 20.0 |
| 12[d,e] | p-Xylene | 160 | 6 | n.d. | [Ru(COD)Cl$_2$] | 0.20 | depe | 0.20 | 16.6 | 29.5 |
| 13[d] | p-Xylene | 160 | 6 | n.d. | [Ru(COD)methylallyl$_2$] | 0.20 | tBuPPyP | 0.20 | 19.5 | 25.2 |
| 15 | Toluene | 155 | 6 | 38 | [Ir(COD)Cl]$_2$ | 0.10 | Triphos | 0.20 | 2.4 | 1.3 |
| 16 | Toluene | 155 | 6 | 42 | [Ir(COD)Cl]$_2$ | 0.10 | Xantphos | 0.20 | 11.6 | 48.8 |

[a]50 ml of solvent; batch size: 50 mmol of octanol, reaction time: 12 h;
[b]evaluation by means of GC (area %); c) product selectivity to n-octylamine determined by means of GC (area %);
[d]10 ml of solvent; batch size: 25 mmol of substrate;
[e]addition of 0.4 mol% of KOtBu (based on octanol);
[f]molar equivalents of $NH_3$ per OH function on the substrate.

TABLE 1b

| No[a] | Solvent | T [°C.] | $NH_3$ [Eq.][d] | Reaction pressure [bar] | Metall salt [M] | Met. [M] (mol %) | Ligand [L] | Lig. [L] (mol %) | Conversion[b] | Selectivity[c] |
| --- | --- | --- | --- | --- | --- | --- | --- | --- | --- | --- |
| 1 | Toluol | 180 | 6 | 41.8 | [RuHCl(CO)(PPh$_3$)$_3$] | 0.10 | DPPEPP | 0.10 | 91.5 | 81.8 |
| 2 | Toluol | 155 | 6 | 43.2 | [Ru(COD)Cl$_2$] | 0.10 | t-Bu-Xantphos | 0.10 | 18.7 | 67.3 |
| 3[e] | Toluol | 155 | 6 | 39.2 | [RuHCl(CO)(PPh$_3$)$_3$] | 0.2 | Triphos | 0.2 | 47.0 | 83.8 |
| 4[f] | Toluol | 155 | 6 | 42.2 | [RuHCl(CO)(PPh$_3$)$_3$] | 0.2 | Triphos | 0.2 | 70.4 | 84.5 |
| 5[g] | Toluol | 155 | 6 | 43.0 | [RuHCl(CO)(PPh$_3$)$_3$] | 0.2 | Triphos | 0.2 | 50.7 | 85.6 |

TABLE 1b-continued

| No[a] | Solvent | T [°C.] | NH₃ [Eq.][d] | Reaction pressure [bar] | Metall salt [M] | Met. [M] (mol %) | Ligand [L] | Lig. [L] (mol %) | Conversion[b] | Selectivity[c] |
|---|---|---|---|---|---|---|---|---|---|---|
| 6[h] | Toluol | 155 | 6 | 42.1 | [RuHCl(CO)(PPh₃)₃] | 0.2 | Triphos | 0.2 | 67.2 | 85.9 |
| 7 | THF | 155 | 6 | 39.9 | [RuHCl(CO)(PPh₃)₃] | 0.2 | dppb | 0.2 | 35.2 | 75.2 |

[a] 50 ml solvent; batch size: 50 mmol octanol, reaction time: 12 h;

[b] evaluation by GC (% by area);

[c] product selectivity to n-octylamine determined by GC (% by area);

[d] molar equivalents NH₃ per OH function on the substrate;

[e] addition of 50 mmol H₂O;

[f] addition of 50 mmol hexylamine;

[g] addition of 25 mmol H₂O;

[h] addition of 25 mmol hexylamine

TABLE 2

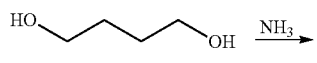

| No.[a] | T [°C.] | NH₃ [EQ.][e] | Reaction pressure [bar] | Metal salt [M] | Met. [M] (mol %)[f] | Ligand [L] | Lig. [L] (mol %)[f] | Conversion[b] | Selectivity[c] a : b : c | | |
|---|---|---|---|---|---|---|---|---|---|---|---|
| 1 | 155 | 6 | 49 | [RuHCl(CO)(PPh₃)₃] | 0.1 | Triphos | 0.1 | 74.7 | 59.1 | 0.7 | 6.7 |
| 2 | 155 | 6 | 66[d] | [RuHCl(CO)(PPh₃)₃] | 0.1 | Triphos | 0.1 | 61.8 | 78.0 | 0.6 | 5.4 |
| 3 | 180 | 6 | 49 | [RuHCl(CO)(PPh₃)₃] | 0.2 | Triphos | 0.2 | 99.9 | 1.7 | 4.7 | 37.7 |
| 4 | 155 | 6 | 45 | [RuHCl(CO)(PPh₃)₃] | 0.1 | Xantphos | 0.1 | 35.0 | 81.8 | 0.0 | 6.4 |
| 5 | 155 | 6 | 47 | [Ru(COD)methylallyl₂] | 0.1 | Tetraphos | 0.1 | 6.0 | 8.5 | 0.0 | 1.6 |
| 6 | 155 | 6 | 39 | [RuHCl(CO)(PPh₃)₃] | 0.2 | Rhodaphos | 0.2 | 39.8 | 17.5 | 0.0 | 4.6 |
| 7 | 155 | 6 | 38 | [RuHCl(CO)(PPh₃)₃] | 0.2 | DPPEPP | 0.2 | 66.6 | 68.1 | 0.1 | 11.0 |

[a] 50 ml of toluene; batch size: 25 mmol of 1,4-butanediol, reaction time: 12 h;

[b] evaluation as per GC (area %);

[c] product selectivity determined by means of GC (area %);

[d] injected cold: 5 bar of H₂, 8 bar of NH₃;

[e] molar equivalents of NH₃ per OH function on the substrate;

[f] mol% based on the number of OH functions on the substrate.

TABLE 3

| No.[a] | T [°C.] | NH₃ [Eq.][e] | Reaction pressure [bar] | Metal salt [M] | Met. [M] (mol %)[f] | Ligand [L] | Lig. [L] (mol%)[f] | Conversion[d] | Selectivity[c] a : b : c | | |
|---|---|---|---|---|---|---|---|---|---|---|---|
| 1 | 155 | 6 | 41 | [RuHCl(CO)(PPh₃)₃] | 0.1 | Triphos | 0.1 | 51.0 | 66.2 | 0.9 | 5.9 |
| 2 | 155 | 6 | 59[d] | [RuHCl(CO)(PPh₃)₃] | 0.1 | Triphos | 0.1 | 16.2 | 87.3 | 0.1 | 2.3 |
| 3 | 180 | 6 | 41 | [RuHCl(CO)(PPh₃)₃] | 0.2 | Triphos | 0.2 | 97.6 | 26.4 | 13.4 | 54.0 |
| 4 | 180 | 6 | 43 | [RuHCl(CO)(PPh₃)₃] | 0.2 | Xantphos | 0.1 | 27.7 | 67.1 | 0.2 | 5.3 |
| 5 | 155 | 6 | 44 | [Ru(COD)methylallyl₂] | 0.1 | Tetraphos | 0.1 | 3.9 | 0.0 | 0.0 | 1.1 |
| 6 | 155 | 6 | 40 | [RuHCl(CO)(PPh₃)₃] | 0.2 | Rhodaphos | 0.2 | 21.8 | 4.8 | 0.0 | 1.3 |
| 7 | 155 | 6 | 38 | [RuHCl(CO)(PPh₃)₃] | 0.2 | DPPEPP | 0.2 | 21.5 | 46.0 | 0.0 | 1.8 |

[a] 50 ml of toluene; batch size: 25 mmol of diethylene glycol, reaction time: 12 h;

[b] evaluation as per GC (area %);

[c] product selectivity determined by means of GC (area %);

[d] injected cold: 5 bar of H₂, 8 bar of NH₃;

[e] molar equivalents of NH₃ per OH function on the substrate;

[f] mol% based on the number of OH functions on the substrate.

TABLE 4

$$HO\underset{n}{\frown}OH \xrightarrow{NH_3} HO\underset{n}{\frown}NH_2 + H_2N\underset{n}{\frown}NH_2$$
$$\hspace{4cm} a \hspace{3cm} b$$

| No[a] | Substrate | T [°C.] | Time [t] | NH₃ [Eq.][e] | Reaction pressure [bar] | Solvent (waterfree) | Metall salt [M] | Met. [M] (mol %)[f] | Ligand [L] | Lig. [L] (mol %)[f] | Conversion[b] | Selectivity[c] a : b | |
|---|---|---|---|---|---|---|---|---|---|---|---|---|---|
| 1 | 1,6-hexanediol | 155 | 12 | 6 | 42 | Toluol | [RuHCl(CO)(PPh₃)₃] | 0.10 | Triphos | 0.10 | 83.0 | 61.3 | 25.7 |
| 2 | 1,6-hexanediol | 155 | 12 | 6 | 36 | Toluol | [RuHCl(CO)(PPh₃)₃] | 0.10 | Xantphos | 0.10 | 33.4 | 84.9 | 4.6 |
| 3 | 1,6-hexanediol | 155 | 12 | 6 | 40 | Toluol | [RuHCl(CO)(PPh₃)₃] | 0.10 | DPPEPP | 0.10 | 70.7 | 66.5 | 16.0 |
| 4 | 1,6-hexanediol | 155 | 12 | 6 | 44 | Toluol | [RuHCl(CO)(PPh₃)₃] | 0.10 | Rhodaphos | 0.10 | 35.1 | 53.0 | 2.0 |
| 5 | 1,10-decandiol | 155 | 24 | 6 | 39 | Toluol | [RuHCl(CO)(PPh₃)₃] | 0.20 | Triphos | 0.20 | 85.7 | 43.0 | 44.4 |
| 6 | 1,10-decandiol | 180 | 24 | 6 | 43 | Toluol | [RuHCl(CO)(PPh₃)₃] | 0.20 | Triphos | 0.20 | 93.3 | 2.0 | 90.1 |
| 7[d] | 1,9-nonanediol | 155 | 24 | 12 | 14 | Mesitylen | [RuHCl(CO)(PPh₃)₃] | 0.20 | Triphos | 0.20 | 79.3 | 54.0 | 31.1 |

[a] 50 ml solvent; batch size: 25 mmol diol;
[b] evaluation by GC (% by area);
[c] product selectivity determined by means of GC (% by area);
[d] batch size: 50 mmol substrate;
[e] molar equivalent NH₃ per OH function on the substrate;
[f] mol % based on the number of OH functions on the substrate

TABLE 5

$$HO\underset{}{\frown}O\underset{}{\frown}OH \xrightarrow{NH_3} H_2N\underset{}{\frown}O\underset{}{\frown}OH + H_2N\underset{}{\frown}O\underset{}{\frown}NH_2$$
$$\hspace{5cm} a \hspace{3cm} b$$

| No[a] | Substrate | T [°C.] | Time [t] | conc. [mol/l] | NH₃ [Eq.][d] | Reaction pressure [bar] | Solvent (waterfree) | Metal salt [M] | Met. [M] (mol %)[e] | Ligand [L] | Lig. [L] (mol %)[e] | Conversion[b] | Selectivity[c] a : b | |
|---|---|---|---|---|---|---|---|---|---|---|---|---|---|---|
| 1 | 2,5-dimethanolfuran | 140 | 24 | 1 | 6 | 15 | THF | [RuHCl(CO)(PPh₃)₃] | 0.20 | Triphos | 0.20 | 46.8 | 63.1 | 10.2 |

[a] 40 ml solvent; batch size: 40 mmol diol;
[b] evaluation by GC (% by area);
[c] product selectivity determined by means of GC (% by area);
[d] molar equivalents NH₃ per OH function on the substrate;
[e] mol % based on the number of OH functions on the substrate

The invention claimed is:

1. A process for producing a primary amine comprising a functional group having a formula of —CH₂—NH₂, the process comprising:

aminating a starting material comprising a functional group having a formula of —CH₂—OH with ammonia, thereby eliminating water, to obtain the primary amine, wherein the aminating is homogeneously catalyzed in the presence of a complex catalyst comprising at least one element selected from groups 8 and 9 of the Periodic Table of the Elements, and a phosphorus donor ligand of formula (I);

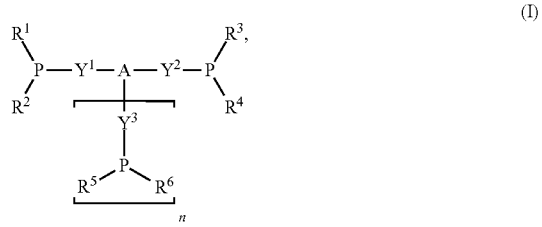

(I)

wherein:

n is 0 or 1;

$R^1, R^2, R^3, R^4, R^5, R^6$ are each independently an unsubstituted or at least monosubstituted $C_1$-$C_{10}$-alkyl, $C_1$-$C_4$-alkyldiphenylphosphine (—$C_1$-$C_4$-alkyl-P(phenyl)₂), $C_3$-$C_{10}$-cycloalkyl, $C_3$-$C_{10}$-heterocyclyl comprising at least one heteroatom selected from the group consisting of N, O, and S, $C_5$-$C_{14}$-aryl, or $C_5$-$C_{10}$-heteroaryl comprising at least one heteroatom selected from the group consisting of N, O, and S, wherein the substituents are selected from the group consisting of F, Cl, Br, OH, CN, NH₂, and a $C_1$-$C_{10}$-alkyl;

A is i) a bridging group selected from the group consisting of an unsubstituted or at least monosubstituted N, O, P, $C_1$-$C_6$-alkane, $C_3$-$C_{10}$-cycloalkane, $C_3$-$C_{10}$-heterocloalkane comprising at least one heteroatom selected from the group consisting of N, O, and S, $C_5$-$C_{14}$-aromatic, and $C_5$-$C_6$-heteroaromatic comprising at least one heteroatom selected from the group consisting of N, O and S, wherein the substituents are selected from the group consisting of a $C_1$-$C_4$-alkyl, phenyl, F, Cl, Br, OH, OR⁷, NH₂, NHR⁷, and N(R⁷)₂, wherein R⁷ is a $C_1$-$C_{10}$-alkyl or a $C_5$-$C_{10}$-aryl, or ii) a bridging group of formula (II) or (III):

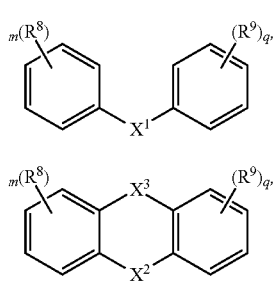

wherein
m, q are each independently 0, 1, 2, 3, or 4,
$R^8$, $R^9$ are each independently selected from the group consisting of a $C_1$-$C_{10}$-alkyl, F, Cl, Br, OH, $OR^7$, $NH_2$, $NHR^7$, and $N(R^7)_2$, wherein $R^7$ is a $C_1$-$C_{10}$-alkyl or a $C_5$-$C_{10}$-aryl,
$X^1$, $X^2$ are each independently NH, O, or S,
$X^3$ is a bond, NH, $NR^{10}$, O, S, or $CR^{11}R^{12}$,
$R^{10}$ is a an unsubstituted or at least monosubstituted $C_1$-$C_{10}$-alkyl, $C_3$-$C_{10}$-cycloalkyl, $C_3$-$C_{10}$-heterocyclyl comprising at least one heteroatom selected from the group consisting of N, O, and S, $C_5$-$C_{14}$-aryl, or $C_5$-$C_{10}$-heteroaryl comprising at least one heteroatom selected from the group consisting of N, O, and S, wherein the substituents are selected from the group consisting of F, Cl, Br, OH, CN, $NH_2$, and a $C_1$-$C_{10}$-alkyl,
$R^{11}$, $R^{12}$ are each independently an unsubstituted or at least monosubstituted $C_1$-$C_{10}$-alkyl, $C_3$-$C_{10}$-cycloalkyl, $C_3$-$C_{10}$-cycloalkoxy, $C_3$-$C_{10}$-heterocyclyl comprising at least one heteroatom selected from the group consisting of N, O, and S, $C_5$-$C_{14}$-aryl, $C_5$-$C_{14}$-aryloxy, or $C_5$-$C_{10}$-heteroaryl comprising at least one heteroatom selected from the group consisting of N, O, and S, wherein the substituents are selected from the group consisting of F, Cl, Br, OH, CN, $NH_2$, and $C_1$-$C_{10}$-alkyl; and
$Y^1$, $Y^2$, $Y^3$ are each independently a bond, or an unsubstituted or at least monosubstituted methylene, ethylene, trimethylene, tetramethylene, pentamethylene, or hexamethylene, wherein the substituents are selected from the group consisting of F, Cl, Br, OH, $OR^7$, CN, $NH_2$, $NHR^7$, $N(R^7)_2$, and a $C_1$-$C_{10}$-alkyl, and wherein $R^7$ is a $C_1$-$C_{10}$-alkyl or a $C_5$-$C_{10}$-aryl.

2. The process of claim 1, wherein
$R^1$, $R^2$, $R^3$, $R^4$, $R^5$, $R^6$ are each independently an unsubstituted $C_1$-$C_{10}$-alkyl, $C_1$-$C_4$-alkyldiphenylphosphine, $C_3$-$C_{10}$-cycloalkyl, $C_3$-$C_{10}$-heterocyclyl comprising at least one heteroatom selected from the group consisting of N, O, and S, $C_5$-$C_{14}$-aryl, or $C_5$-$C_{10}$-heteroaryl comprising at least one heteroatom selected from the group consisting of N, O, and S;
A is i) a bridging group selected from the group consisting of an unsubstituted N, O, P, $C_1$-$C_6$-alkane, $C_3$-$C_{10}$-cycloalkane, $C_3$-$C_{10}$-heterocycloalkane comprising at least one heteroatom selected from the group consisting of N, O, and S, $C_5$-$C_{14}$-aromatic, and $C_5$-$C_6$-heteroaromatic comprising at least one heteroatom selected from the group consisting of N, O, and S; or ii) a bridging group of the formula II or III:

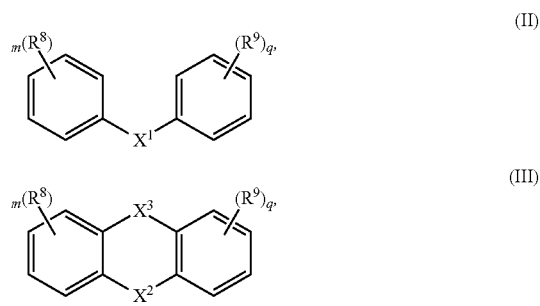

wherein
m, q are each independently 0, 1, 2, 3, or 4,
$R^8$, $R^9$ are each independently selected from the group consisting of a $C_1$-$C_{10}$-alkyl, F, Cl, Br, OH, $OR^7$, $NH_2$, $NHR^7$, and $N(R^7)_2$, wherein $R^7$ is selected from $C_1$-$C_{10}$-alkyl and $C_5$-$C_{10}$-aryl,
$X^1$, $X^2$ are each independently NH, O, or S,
$X^3$ is a bond, NH, $NR^{10}$, O, S, or $CR^{11}R^{12}$,
$R^{10}$ is an unsubstituted $C_1$-$C_{10}$-alkyl, $C_3$-$C_{10}$-cycloalkyl, $C_3$-$C_{10}$-heterocyclyl comprising at least one heteroatom selected from the group consisting of N, O, and S, $C_5$-$C_{14}$-aryl, or $C_5$-$C_{10}$-heteroaryl comprising at least one heteroatom selected from the group consisting of N, O, and S,
$R^{11}$, $R^{12}$ are each independently an unsubstituted $C_1$-$C_{10}$-alkyl, $C_1$-$C_{10}$-alkoxy, $C_3$-$C_{10}$-cycloalkyl, $C_3$-$C_{10}$-cycloalkoxy, $C_3$-$C_{10}$-heterocyclyl comprising at least one heteroatom selected from the group consisting of N, O, and S, $C_5$-$C_{14}$-aryl, $C_5$-$C_{14}$-aryloxy, or $C_5$-$C_{10}$-heteroaryl comprising at least one heteroatom selected from the group consisting of N, O, and S; and
$Y^1$, $Y^2$, $Y^3$ are each independently a bond, an unsubstituted methylene, ethylene, trimethylene, tetramethylene, pentamethylene, or hexamethylene.

3. The process of claim 1, wherein the phosphorus donor ligand has a formula (V):

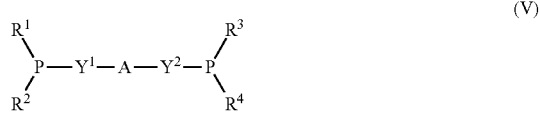

wherein:
$Y^1$, $Y^2$ are each independently a bond, or an unsubstituted or at least monosubstituted methylene, ethylene, trimethylene, tetramethylene, pentamethylene, or hexamethylene, wherein the substituents are selected from the group consisting of F, Cl, Br, OH, $OR^7$, CN, $NH_2$, $NHR^7$, $N(R^7)_2$, and $C_1$-$C_{10}$-alkyl, and wherein $R^7$ is a $C_1$-$C_{10}$-alkyl or a $C_5$-$C_{10}$-aryl.

4. The process of claim 1, wherein the phosphorus donor ligand has a formula (VI):

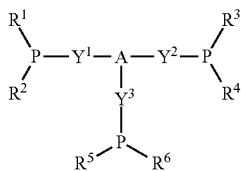

wherein

R$^1$, R$^2$, R$^3$, R$^4$, R$^5$, R$^6$ are each independently an unsubstituted or at least monosubstituted C$_1$-C$_{10}$-alkyl, C$_3$-C$_{10}$-cycloalkyl, C$_3$-C$_{10}$-heterocyclyl comprising at least one heteroatom selected from the group consisting of N, O, and S, C$_5$-C$_{14}$-aryl, or C$_5$-C$_{10}$-heteroaryl comprising at least one heteroatom selected from the group consisting of N, O, and S, wherein the substituents are selected from the group consisting of F, Cl, Br, OH, CN, NH$_2$, and a C$_1$-C$_{10}$-alkyl; and A is a bridging group selected from the group consisting of an unsubstituted or at least monosubstituted N, P, C$_1$-C$_6$-alkane, C$_3$-C$_{10}$-cycloalkane, C$_3$-C$_{10}$-heterocycloalkane comprising at least one heteroatom selected from the group consisting of N, O, and S, C$_5$-C$_{14}$-aromatic, and C$_5$-C$_6$-heteroaromatic comprising at least one heteroatom selected from the group consisting of N, O, and S, wherein the substituents are selected from the group consisting of a C$_1$-C$_4$-alkyl, F, Cl, Br, OH, OR$^7$, NH$_2$, NHR$^7$, and N(R$^7$)$_2$, wherein R$^7$ is a C$_1$-C$_{10}$-alkyl or a C$_5$-C$_{10}$-aryl.

5. The process of claim 1, wherein the phosphorus donor ligand has a formula (IX) or (X),

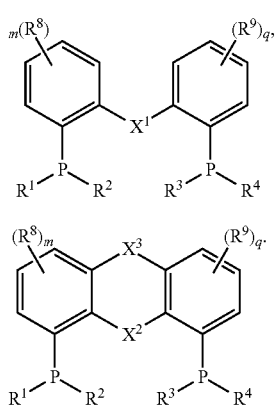

6. The process of claim 1, wherein the complex catalyst comprises at least one element selected from the group consisting of ruthenium and iridium, and at least one phosphorus donor ligand selected from the group consisting of 1,2-bis(diphenylphosphino)ethane (dppe), 1,2-bis(dicyclohexylphosphino)ethane, 1,2-bis(diphenylphosphino)propane (dppp), 1,2-bis(diphenylphosphino)butane (dppb), 2,3-bis(dicyclohexylphosphino)ethane (dcpe), 4,5-bis(diphenylphosphino)-9,9-dimethylxanthene (xantphos), bis(2-diphenylphosphinoethyl)phenylphosphine, and 1,1,1-tris(diphenylphosphinomethyl)ethane (triphos).

7. The process of claim 1, wherein the complex catalyst comprises ruthenium and at least one phosphorus donor ligand selected from the group consisting of 4,5-bis(diphenylphosphino)-9,9-dimethylxanthene (xantphos), bis(2-diphenylphosphinoethyl)phenylphosphine, and 1,1,1-tris(diphenylphosphinomethyl)ethane (triphos).

8. The process of claim 7, wherein the phosphorus donor ligand is selected from the group consisting of bis(2-diphenylphosphinoethyl)phenylphosphine and triphos.

9. The process of claim 1, wherein the complex catalyst comprises iridium and at least one phosphorus donor ligand selected from the group consisting of 4,5-bis(diphenylphosphino)-9,9-dimethylxanthene (xantphos), bis(2-diphenylphosphinoethyl)phenylphosphine, and 1,1,1-tris(diphenylphosphinomethyl)ethane (triphos).

10. The process of claim 1, wherein the starting material comprises at least two functional groups having a formula —CH$_2$—OH.

11. The process of claim 1, wherein the aminating is carried out in the presence of a nonpolar solvent.

12. The process of claim 11, wherein the aminating is carried out in the presence of a solvent selected from the group consisting of saturated hexane, heptane, octane, cyclohexane, benzene, toluene, xylene, mesitylene, THF, diethyl ether, 1,4-dioxane, MTBE, diglyme, and 1,2-dimethoxyethane.

13. The process of claim 1, wherein the aminating is carried out at a temperature in a range from 20 to 250° C. and a pressure from 0.1 to 20 MPas absolute.

14. The process of claim 1, wherein the aminating is carried out in the presence of a base.

15. The process of claim 7, wherein the phosphorus donor ligand is bis(2-diphenylphosphinoethyl)phenylphosphine.

16. The process of claim 7, wherein the phosphorus donor ligand is triphos.

17. The process of claim 9, wherein the phosphorus donor ligand is 4,5-bis(diphenylphosphino)-9,9-dimethylxanthene (xantphos).

18. The process of claim 9, wherein the phosphorus donor ligand is bis(2-diphenylphosphinoethyl)phenylphosphine.

19. The process of claim 9, wherein the phosphorus donor ligand is 1,1,1-tris(diphenylphosphinomethyl)ethane (triphos).

20. The process of claim 11, wherein the nonpolar solvent is selected from the group consisting of toluene, xylene, and mesitylene.

* * * * *